United States Patent
Buchstaller

(10) Patent No.: US 11,026,936 B2
(45) Date of Patent: Jun. 8, 2021

(54) PIPERIDINYL-PROPANONE DERIVATIVES

(71) Applicant: Merck Patent GmbH, Darmstadt (DE)

(72) Inventor: Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 287 days.

(21) Appl. No.: 16/089,463

(22) PCT Filed: Mar. 27, 2017

(86) PCT No.: PCT/EP2017/057168
§ 371 (c)(1),
(2) Date: Sep. 28, 2018

(87) PCT Pub. No.: WO2017/167676
PCT Pub. Date: Oct. 5, 2017

(65) Prior Publication Data
US 2020/0253949 A1   Aug. 13, 2020

(30) Foreign Application Priority Data
Mar. 29, 2016   (EP) .................................. 16162544

(51) Int. Cl.
| A61K 31/4545 | (2006.01) |
| C07D 401/06 | (2006.01) |
| C07D 401/14 | (2006.01) |
| A61K 31/454 | (2006.01) |
| C07D 413/06 | (2006.01) |

(52) U.S. Cl.
CPC ........ *A61K 31/4545* (2013.01); *A61K 31/454* (2013.01); *C07D 401/06* (2013.01); *C07D 401/14* (2013.01); *C07D 413/06* (2013.01)

(58) Field of Classification Search
CPC .. C07D 401/06; C07D 401/14; C07D 413/06; A61K 31/4545
USPC ....................................................... 514/318
See application file for complete search history.

(56) References Cited

U.S. PATENT DOCUMENTS

| 6,979,686 B1 | 12/2005 | Naraian et al. |
| 8,815,882 B2 | 8/2014 | Baker-Glenn et al. |
| 8,871,934 B2 | 10/2014 | Motomura et al. |
| 8,999,966 B2 | 4/2015 | Boga et al. |
| 9,365,539 B2 | 6/2016 | Hale et al. |
| 9,737,537 B2 | 8/2017 | Chen et al. |

FOREIGN PATENT DOCUMENTS

| EP | 2345629 B1 | 6/2015 |
| WO | 2001017942 A1 | 3/2001 |
| WO | 08083238 A2 | 7/2008 |
| WO | 11143057 A1 | 11/2011 |
| WO | 12058127 A2 | 5/2012 |
| WO | 12062783 A1 | 5/2012 |
| WO | 12082947 A1 | 6/2012 |
| WO | 2015090496 A1 | 6/2015 |

OTHER PUBLICATIONS

R.M. mayers AZD7545, a novel inhibitor of pyruvate dehydrogenase kinase 2 (PDHK2), activates pyruvate dehydrogenase in vivo and improves blood glucose control in obese (fa/fa) Zucker rats. (Year: 2003).*
Choong-Hwan Kwak et al Huzhangoside A supresses Tumor Growth through Inhibition of Pyruvate Dehydrogenase Kinase Activity (Year: 2019).*
International Search Report PCT/EP2017/057168 dated May 11, 2018. (pp. 1-2).
T.E. Roche et al., "Pyruvate dehydrogenase kinase regulatory mechanisms and inhibition in treating diabetes, heart ischemia, and cancer" Cell. Mal. Life Sci. 64(2007) 830-849.
A.Kumar et al., "Novel molecular mechanisms of antitumor action of dichloroacetate against T cell lymphoma: Implication of altered glucose metabolism, pH homeostasis and cell survival regulation" Chemico-Biological Interactions 199 (2012), 29-37.
I.Papandreou et al., "Anticancer drugs that target metabolism: is dichloroacetate the new paradigm?" Int. J. Cancer: 128, 1000-1008 (2011).
G. Sutendra et al., "Pyruvatedehydrogenasekinaseasanoveltherapeutictargetinoncology" Frontiers in Oncology, 2013, vol. 3, 1-11.
Office Action in corresponding Cn appln. 201780020671.6 dated Jul. 3, 2020 (pp. 1-6) and english translation thereof (pp. 1-9).

\* cited by examiner

*Primary Examiner* — Rita J Desai
(74) *Attorney, Agent, or Firm* — Millen White Zelano & Branigan

(57) ABSTRACT

Compounds of the formula I

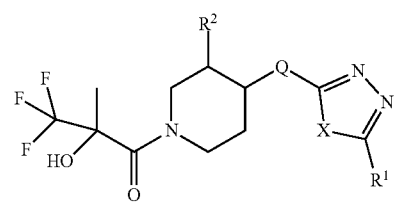

in which X, Q, $R^1$ and $R^2$ have the meanings indicated in Claim 1, are inhibitors of pyruvate dehydrogenase kinase (PDHK), and can be employed, inter alia, for the treatment of diseases such as cancer.

17 Claims, No Drawings

PIPERIDINYL-PROPANONE DERIVATIVES

TECHNICAL FIELD OF THE INVENTION

The present invention relates to novel piperidinyl-propanone derivatives which inhibit pyruvate dehydrogenase kinase (PDHK), to pharmaceutical compositions comprising them, to processes for their preparation, and to their use in therapy for the treatment of cancers.

BACKGROUND OF THE INVENTION

Pyruvate dehydrogenase kinase (also pyruvate dehydrogenase complex kinase, PDC kinase, or PDHK) is a kinase enzyme which acts to inactivate the enzyme pyruvate dehydrogenase by phosphorylating it using ATP.

PDHK thus participates in the regulation of the pyruvate dehydrogenase complex of which pyruvate dehydrogenase is the first component. Both PDHK and the pyruvate dehydrogenase complex are located in the mitochondrial matrix of eukaryotes. The complex acts to convert pyruvate (a product of glycolysis in the cytosol) to acetyl-coA, which is then oxidized in the mitochondria to produce energy, in the citric acid cycle. By downregulating the activity of this complex, PDHK will decrease the oxidation of pyruvate in mitochondria and increase the conversion of pyruvate to lactate in the cytosol.

The opposite action of PDHK, namely the dephosphorylation and activation of pyruvate dehydrogenase, is catalyzed by a phosphoprotein phosphatase called pyruvate dehydrogenase phosphatase.

(Pyruvate dehydrogenase kinase should not be confused with Phosphoinositide-dependent kinase-1, which is also sometimes known as "PDK1".)

There are four known isozymes of PDHK in humans: PDHK1-PDHK4.

Some studies have shown that cells that lack insulin (or are insensitive to insulin) overexpress PDHK4. As a result, the pyruvate formed from glycolysis cannot be oxidized which leads to hyperglycaemia due to the fact that glucose in the blood cannot be used efficiently. Therefore several drugs target PDHK4 hoping to treat type II diabetes.

PDHK1 has shown to have increased activity in hypoxic cancer cells due to the presence of HIF-1. PDHK1 shunts pyruvate away from the citric acid cycle and keeps the hypoxic cell alive. Therefore, PDHK1 inhibition has been suggested as an antitumor therapy since PDHK1 prevents apoptosis in these cancerous cells. Similarly, PDHK3 has been shown to be overexpressed in colon cancer cell lines. Three proposed inhibitors are AZD7545 and dichloroacetate which both bind to PDHK1, and Radicicol which binds to PDHK3.

Increasing PDC in the active form by inhibiting PDHK activity is a drug target for diabetes, heart disease and cancer.

EP 2 345 629 A1 discloses PDHK inhibitors which are considered to be useful for the treatment or prophylaxis of diseases relating to glucose utilization disorder, for example, diabetes (e.g., type 1 diabetes, type 2 diabetes etc.), insulin resistance syndrome, metabolic syndrome, hyperglycemia and hyperlactacidemia. In addition, a PDHK inhibitor is considered to be useful for the treatment or prophylaxis of diabetic complications (e.g., neuropathy, retinopathy, nephropathy, cataract etc.). Furthermore, a PDHK inhibitor is considered to be useful for the treatment or prophylaxis of diseases caused by limited energy substrate supply to the tissues, for example, cardiac failure, cardiomyopathy, myocardial ischemia, dyslipidemia and atherosclerosis. Additionally, a PDHK inhibitor is considered to be useful for the treatment or prophylaxis of cerebral ischemia or cerebral apoplexy. Moreover, a PDHK inhibitor is considered to be useful for the treatment or prophylaxis of mitochondrial disease, mitochondrial encephalomyopathy, cancer and the like. Also, it is considered to be useful for the treatment or prophylaxis of pulmonary hypertension.

LITERATURE

Wikipedia, pyruvate dehydrogenase kinase;
T. E. Roche et al., Cell. Mol. Life Sci. 64 (2007) 830-849;
A. Kumar et al., Chemico-Biological Interactions 199 (2012) 29-37;
I. Papandreou et al., Int. J. Cancer: 128, 1001-1008 (2011);
G. Sutendra et al., frontiers in oncology, 2013, vol. 3, 1-11.

The invention had the object of finding novel compounds having valuable properties, in particular those which can be used for the preparation of medicaments.

It has been found that the compounds according to the invention and salts thereof have very valuable pharmacological properties while being well tolerated.

The present invention specifically relates to compounds of the formula I which inhibit PDHK, preferably PDHK2, to compositions which comprise these compounds, and to processes for the use thereof for the treatment of PDHK-induced diseases and complaints.

The compounds of the formula I can furthermore be used for the isolation and investigation of the activity or expression of PDHK. In addition, they are particularly suitable for use in diagnostic methods for diseases in connection with unregulated or disturbed PDHK activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Fluorene derivatives are described as PDHK inhibitors for the treatment of diseases such as diabetes and cancer in EP 2 345 629 A1.

Other pyrazole derivatives for use as TGR5 agonists are disclosed in WO 2012/082947.

The preparation of pyrazolylaminopyrimidine derivatives for use as LRRK2 modulators is described in WO 2012/062783.

The preparation of phenylmethyl-piperidinyl-triazolyl-pyridinyl-indazole derivatives for use as ERK inhibitors is described in WO 2012/058127.

The preparation of substituted pyrazoles and triazoles as novel prolylcarboxypeptidase inhibitors is described in WO 2011/143057.

Substituted piperidinylthiazole derivatives and analogs for the treatment of diabetes and metabolic disorders are disclosed in WO 2008/083238.

Heteroarylpyrazoles as p38 kinase inhibitors are described in U.S. Pat. No. 6,979,686 B1.

SUMMARY OF THE INVENTION

The invention relates to compounds of the formula I

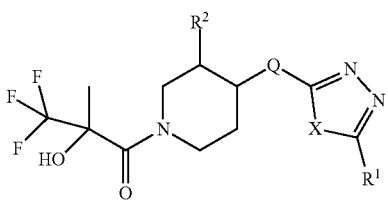

in which
X denotes NH or O,
Q denotes C(CH$_3$)$_2$ or 1,1-cyclopropylene,
R$^1$ denotes H, A, Cyc, Ar or Het,
R$^2$ denotes H or CH$_3$,
R$^3$ denotes H or A',
Ar denotes phenyl, which is unsubstituted or mono-, di- or trisubstituted by Hal, NO$_2$, CN, A, OR$^3$, S(O)$_m$R$^3$, N(R$^3$)$_2$, COA, COOR$^3$, CON(R$^3$)$_2$, SO$_2$N(R$^3$)$_2$, NR$^3$COR$^3$, NR$^3$SO$_2$A and/or NR$^3$CON(R$^3$)$_2$,
Het denotes a mono- or bicyclic saturated, unsaturated or aromatic heterocycle having 1 to 4 N, O and/or S atoms, which is unsubstituted or mono- or disubstituted by Hal, NO$_2$, CN, A, OR$^3$S(O)$_m$R$^3$, N(R$^3$)$_2$, COA, COOR$^3$, CON(R$^3$)$_2$, SO$_2$N(R$^3$)$_2$, NR$^3$COR$^3$, NR$^3$SO$_2$A and/or NR$^3$CON(R$^3$)$_2$,
A denotes unbranched or branched alkyl with 1-10 C-atoms, wherein one or two non-adjacent CH- and/or CH$_2$-groups may be replaced by N-, O- and/or S-atoms and/or wherein 1-7 H-atoms may be replaced by R$^4$,
R$^4$ denotes F, Cl or OH,
A' denotes unbranched or branched alkyl with 1-6 C-atoms, wherein 1-5 H-atoms may be replaced by F,
Cyc denotes cyclic alkyl with 3, 4, 5, 6 or 7 C-atoms, which is unsubstituted or monosubstituted by OH,
Hal denotes F, Cl, Br or I,
m denotes 0, 1 or 2,
and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides. It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, wherein X denotes NH,
characterised in that
a compound of the formula II

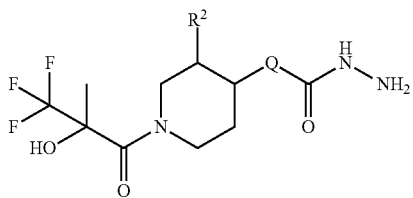

in which Q and $R^2$ have the meanings indicated in Claim 1, is reacted with a compound of the formula III $R^1$—C(=NH)OCH$_3$     III

in which $R^1$ has the meanings indicated in claim 1,
and/or
a base or acid of the formula I is converted into one of its salts.

Above and below, the radicals X, Q, $R^1$ and $R^2$ have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A preferably denotes unbranched or branched alkyl with 1-10 C-atoms, wherein one or two non-adjacent CH- and/or CH$_2$-groups may be replaced by N- and/or O-atoms and wherein 1-7 H-atoms may be replaced by $R^4$.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A denotes preferably CH$_2$OCH$_3$, CH$_2$CH$_2$OH or CH$_2$CH$_2$OCH$_3$. Cyc denotes cyclopropyl, cyclobutyl, cyclopentyl, cyclohexyl or cycloheptyl, preferably unsubstituted or monosubstituted by OH.

A' denotes alkyl, this is unbranched (linear) or branched, and has 1, 2, 3, 4, 5 or 6 C atoms. A' preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A' very particularly preferably denotes alkyl having 1, 2, 3, 4, 5 or 6 C atoms, wherein 1-3 H-atoms may be replaced by F.

$R^1$ preferably denotes A, Cyc, Ar or Het.
$R^3$ preferably denotes H or methyl, most preferably H.

Ar denotes preferably o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxy-carbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, which is unsubstituted or mono-, di- or trisubstituted by Hal, A and/or OR$^3$.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, triazolyl, oxadiazolyl or thiadiazolyl, each of which is unsubstituted or mono- or disubstituted by Hal, A, CN and/or $OR^3$.

Furthermore, Het preferably denotes pyrimidyl, pyridyl, pyridazinyl or pyrazinyl, each of which is unsubstituted or mono- or disubstituted by A and/or $OR^3$.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

The preferred configuration at the chiral alcohol is R.

Accordingly, the invention relates, in particular, to the compounds of the formula I in which at least one of the said radicals has one of the preferred meanings indicated above. Some preferred groups of compounds may be expressed by the following sub-formulae Ia to Ih, which conform to the formula I and in which the radicals not designated in greater detail have the meaning indicated for the formula I, but in which

| | | |
|---|---|---|
| in Ia | $R^1$ | denotes A, Cyc, Ar or Het; |
| in Ib | $R^3$ | denotes H or $CH_3$; |
| in Ic | Ar | denotes phenyl, which is unsubstituted or mono-, di- or trisubstituted by Hal, A and/or $OR^3$; |
| in Id | Het | denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, triazolyl, oxadiazolyl or thiadiazolyl, each of which is unsubstituted or mono- or disubstituted by Hal, A, CN and/or $OR^3$; |
| in Ie | Het | denotes pyrimidyl, pyridyl, pyridazinyl or pyrazinyl, each of which is unsubstituted or mono- or disubstituted by A and/or $OR^3$; |
| in If | A | denotes denotes unbranched or branched alkyl with 1-6 C-atoms, wherein 1-5 H-atoms may be replaced by F; |
| in Ig | Cyc | denotes cyclic alkyl with 3, 4, 5, 6 or 7 C-atoms; |
| in Ih | X | denotes NH or O, |
| | Q | denotes $C(CH_3)_2$ or 1,1-cyclopropylene, |
| | $R^1$ | denotes A, Cyc, Ar or Het, |
| | $R^2$ | denotes H or $CH_3$, |
| | $R^3$ | denotes H or $CH_3$, |
| | Ar | denotes phenyl, which is unsubstituted or mono-, di- or trisubstituted by Hal, A and/or $OR^3$, |
| | Het | denotes pyrimidyl, pyridyl, pyridazinyl or pyrazinyl, each of which is unsubstituted or mono- or disubstituted by A and/or $OR^3$, |
| | A | denotes unbranched or branched alkyl with 1-6 C-atoms, wherein 1-5 H-atoms may be replaced by F, |
| | Cyc | denotes cyclic alkyl with 3, 4, 5, 6 or 7 C-atoms, |
| | Hal | denotes F, Cl, Br or I, | and pharmaceutically acceptable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds for the preparation of compounds of formula I are generally known. If they are novel, however, they can be prepared by methods known per se.

Compounds of the formula I, wherein X denotes NH, can preferably be obtained by reacting a compound of the formula II, with a compound of the formula III.

The reaction is generally carried out in the presence of an acid-binding agent, preferably an organic base, such as N-ethyldiisopropylamine, triethylamine, dimethylaniline, pyridine or quinoline.

Depending on the conditions used, the reaction time is between a few minutes and 14 days, the reaction temperature is between about −30° and 140°, normally between 0° and 110°, in particular between about 20° and about 100°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, acetonitrile, dichloromethane and/or DMF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphor-sulfonate, caprylate, chloride, chlorobenzoate, citrate, cyclopentane-propionate, digluconate, dihydrogenphosphate, dinitrobenzoate, dodecyl-sulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphos-phate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodi-ment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds of the formula I and pharmaceutically acceptable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the pharmaceutically acceptable salts, tautomers and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmeth-acrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, poly-acetals, polydihydroxypyrans, polycyanoacrylates and crosslinked or amphi-pathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, tautomers and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits PDHK in a cell, such as, for example, in vitro or in vivo. In some embodiments, the effective amount of the compound of formula (I) inhibits PDHK in a cell by 10%, 20%, 30%, 40%, 50%, 60%, 70%, 80%, 90% or 99%, compared to the activity of PDHK in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present invention specifically relates to compounds for use of the formula I and pharmaceutically acceptable salts, tautomers and stereoisomers thereof, including mixtures thereof in all ratios, for the treatment of cancer, diabetes and heart ischemia.

Moreover, the present invention relates to compounds for use of the formula I and pharmaceutically acceptable salts, tautomers and stereoisomers thereof, including mixtures thereof in all ratios, for the treatment of insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy.

The present invention specifically relates to methods for treating or preventing cancer, diabetes and heart ischemia, comprising administering to a subject in need thereof an effective amount of a compound of formula I or a pharmaceutically acceptable salt, tautomer, stereoisomer or solvate thereof.

Also encompassed is the use of the compounds of the formula I and/or pharmaceutically acceptable salts, tautomers and stereoisomers thereof for the preparation of a medicament for the treatment or prevention of a PDHK-induced disease or a PDHK-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "PDHK-induced diseases or conditions" refers to pathological conditions that depend on the activity of PDHK. Diseases associated with PDHK activity include cancer, diabetes and heart ischemia.

The present invention specifically relates to compounds for use of the formula I and pharmaceutically acceptable salts, tautomers and stereoisomers thereof, including mixtures thereof in all ratios, for the treatment of diseases in which the inhibition, regulation and/or modulation inhibition of PDHK plays a role.

The present invention specifically relates to compounds of the formula I and pharmaceutically acceptable salts, tautomers and stereoisomers thereof, including mixtures thereof in all ratios, for the use for the inhibition of PDHK.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, representative cancers that compounds of formula I are useful for treating or preventing include cancer of brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechlore-tamine, carboquone; apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/AntaConists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];
Photosensitizers
such as methoxsalen[3];
porfimer sodium, talaporfin, temoporfin;
Antibodies
such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];
catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];
Cytokines
such as aldesleukin, interferon alfa[2], interferon alfa2a[3], interferon alfa2b[2,3]; celmoleukin, tasonermin, teceleukin, oprelvekin[1,3], recombinant interferon beta-1a[4];
Drug Conjugates
such as denileukin diftitox, ibritumomab tiuxetan, iobenguane I123, prednimustine, trastuzumab emtansine, estramustine, gemtuzumab, ozogamicin, aflibercept;
cintredekin besudotox, edotreotide, inotuzumab ozogamicin, naptumomab estafenatox, oportuzumab monatox, technetium (99mTc) arcitumomab[1,3], vintafolide[1,3];
Vaccines
such as sipuleucel[3]; vitespen[3], emepepimut-S[3], oncoVAX[4], rindopepimut[3], troVax[4], MGN-1601[4], MGN-1703[4];
Miscellaneous
alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1] Prop. INN (Proposed International Nonproprietary Name)
[2] Rec. INN (Recommended International Nonproprietary Names)
[3] USAN (United States Adopted Name)
[4] no INN.

The following abbreviations refer respectively to the definitions below:
aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), CDCl$_3$ (deuterated chloroform), CD$_3$OD (deuterated methanol), CH$_3$CN (acetonitrile), c-hex (cyclohexane), d (day), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays
Abbreviations:
GST=Glutathione-S-transferase
FRET=Fluorescence resonance energy transfer
HTRF®=(homogenous time resolved fluorescence)
HEPES=4-(2-hydroxyethyl)-1-piperazine ethanesulfonic acid buffer
DTT=Dithiothreitol
BSA=bovine serum albumin CHAPS=3-[(3-cholamidopropyl)dimethylammonio]-1-propanesulfonate Biochemical Activity Testing of PDHK2: PDC Inactivation Assay The biochemical activity assay for PDHK2 is based on the inactivation of PDC through phosphorylation by PDHK2. The assay is run in two steps: the enzymatic PDHK2 reaction in which isolated PDC is phosphorylated by PDHK2 with ATP as co-substrate and the PDC activity assay in which pyruvate and NAD are converted to acetyl-CoA and NADH. The PDC activity correlates to the increase in NADH and thereby is detectable directly via the increasing fluorescence signal (Exc 340 nm, Em 450 nm). Inhibition of PDHK2 results in a lower phosphorylation status and thereby a less decrease in activity of PDC and a stronger increase in NADH fluorescence signal.

The PDC inactivation assay is performed in Greiner 384-well microtiter plates and is used for high throughput screen. 4 μl of PDHK2 (human, rec, Carna Bioscience, 10 ng/μl-137 nM final concentration) and PDC (isolated from porcine heart, Sigma-Aldrich, 20 mU/ml final concentration) are incubated in the absence or presence of the test compound (10 dilution concentrations) for 30 min at room temperature in kinase buffer (15 mM potassium phosphate buffer, pH 7.0, 60 mM KCl, 1.5 mM DTT, 2.5 mM MgCl$_2$, 0.0125% (w/v) BSA, 0.125% Pluronic F-68). The kinase reaction is started by the addition of 4 μl ATP substrate solution (fc 5 μM in kinase buffer). After 30 min incubation at 37° C. 40 μl of PDC reaction solution (100 mM Tris/HCl, pH 7.8, 0.5 mM EDTA, 1 mM MgCl$_2$, 50 mM NaF, 0.25 mM Coenzyme A, 5 mM pyruvate, 1 mM NAD, 5 mM DTT, 1 mM thiamine pyrophosphate) is added. The first fluorescence measurement is performed on a Perkin Elmer Envision (Exc 340 nm, Em 450 nm). The reaction is incubated for 45 min at room temperature. Afterwards a second fluorescence measurement is performed and the PDC activity is calculated by the difference between both measurements. As full value for the PDHK2 assay the inhibitor-free PDHK2 reaction is used. The pharmacological zero value used is DCA (Sigma-Aldrich) in a final concentration of 3 mM. The inhibitory values (IC50) were determined using either the program Symyx Assay Explorer® or Condosseo® from GeneData.

Isothermal Titration Calorimetry

ITC measurements were performed with a VP-ITC micro calorimeter (Microcal, LLC/GE Healthcare Bio-Sciences AB, Uppsala, Sweden). In general titrations were performed by titrating the protein (50 μM) to the test compound (5 μM) in 12 μl injections. All binding experiments were carried out at 30° C. In general the test compounds were diluted form DMSO stock solutions into the measurement buffer with a maximum final concentration of 1% DMSO. The measurement buffer was 20 mM HEPES, 135 mM KCl, 1 mM TCEP, 2 mM $MgCl_2$, 15 mM $NaH_2PO_4$, pH 7.5. The human PDHK2 (12-407) was produced in E. coli as his-tagged protein and purified by affinity chromatography. The tag was removed by side specific proteolysis. Before titration the protein buffer was changed to the measurement buffer containing the same DMSO concentration as the test compound dilution. ITC data analysis was performed using Origin 7 calorimetry software from the same supplier. For most measurements a binding model of one binding site was assumed. According to the applied mathematical model it is possible to calculate the binding constant ($K_A$), the observed binding enthalpy ($\Delta H^{obs}$) as well as the stoichiometry (N) of the formed complex. Preceding analysis the raw data was corrected for the heats of dilution by extrapolating from the saturation value from the end of titration. In order to allow for direct comparison between the respective experimental series and protein preparations the protein concentration was corrected by referencing titrations to a well behaved standard inhibitor. The apparent stoichiometry values defined the fraction of binding competent protein and compensated for relative errors in protein concentration measurements. This corrected protein concentration was used to set up ITC experiment series with test compounds. Any deviations from ideal 1:1 stoichiometry observed here were attributed to errors in compound concentration. This nominal compound concentration was corrected as well to achieve 1:1 stoichiometry in the fit.

Cellular Assay for Determination of Compound Activities

Compound activities were determined in a cellular immunofluorescence assay. Human HEK293T cells were seeded into black 384-well plates with clear bottom and grown overnight.

Next day, test compounds were added to the wells and the plates incubated for 5 hours. Following this, cells were fixed with formaldehyde, permeabilised and blocked. The primary antibody, Anti-PDH-E1alpha (pSer300), AP1064 (Merck Millipore) was added and incubated overnight in the plate wells. Next, cells were washed and the seconday antibody, Alexa Fluor 488, goat anti-rabbit ab (A-11008, Invitrogen) was added together with Hoechst 33258 (H3569, Invitrogen) and incubated for 1 hour in the plate wells. Finally, cells were washed and the plates were measured on the laser scanning cytometer acumen hci (TTpLabtech).

The raw data were normalized against a pharmacological inhibitor control and dose response curves were generated by plotting the percent effect values using the software package Genedata screener (Genedata).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation.

$^1$H NMR was recorded on Bruker DPX-300, DRX-400, AVII-400 or BRUKER 500 MHz spectrometer, using residual signal of deuterated solvent as internal reference. Chemical shifts (δ) are reported in ppm relative to the residual solvent signal (δ=2.49 ppm for $^1$H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

Absolute configurations have been determined by X-ray structure analysis.

Pyrazolyl-Piperidine Derivatives: Synthesis Protocols
HPLC/MS-Method:
Gradient: 3.3 min; Flow: 2.4 mL/min von 0 min 4% B, 2.8 min 100% B, 3.3 min 100% B
A: Water+HCOOH (0.05% Vol.); B: Acetonitrile+HCOOH (0.04% Vol.)
Column: Chromolith SpeedROD RP 18e 50-4.6
Wave length: 220 nm

EXAMPLE 1

(R)-3,3,3-Trifluoro-2-hydroxy-2-methyl-1-{4-[1-(5-phenyl-1H-[1,2,4]triazol-3-yl)-cyclopropyl]-piperidin-1-yl}-propan-1-one ("A1")

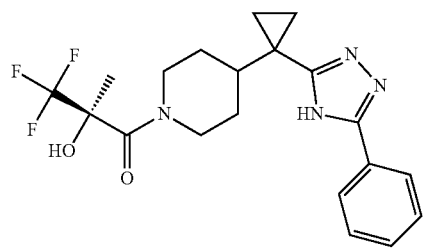 [SMILES: C[C@@](O)(C(=O)N1CCC(C2(c3nnc(-c4ccccc4)[nH]3)CC2)CC1)C(F)(F)F]

Reaction Scheme:

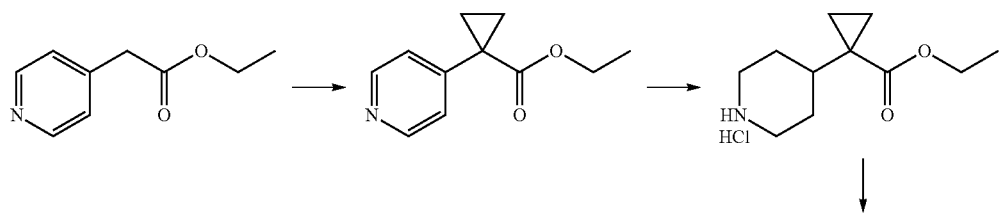

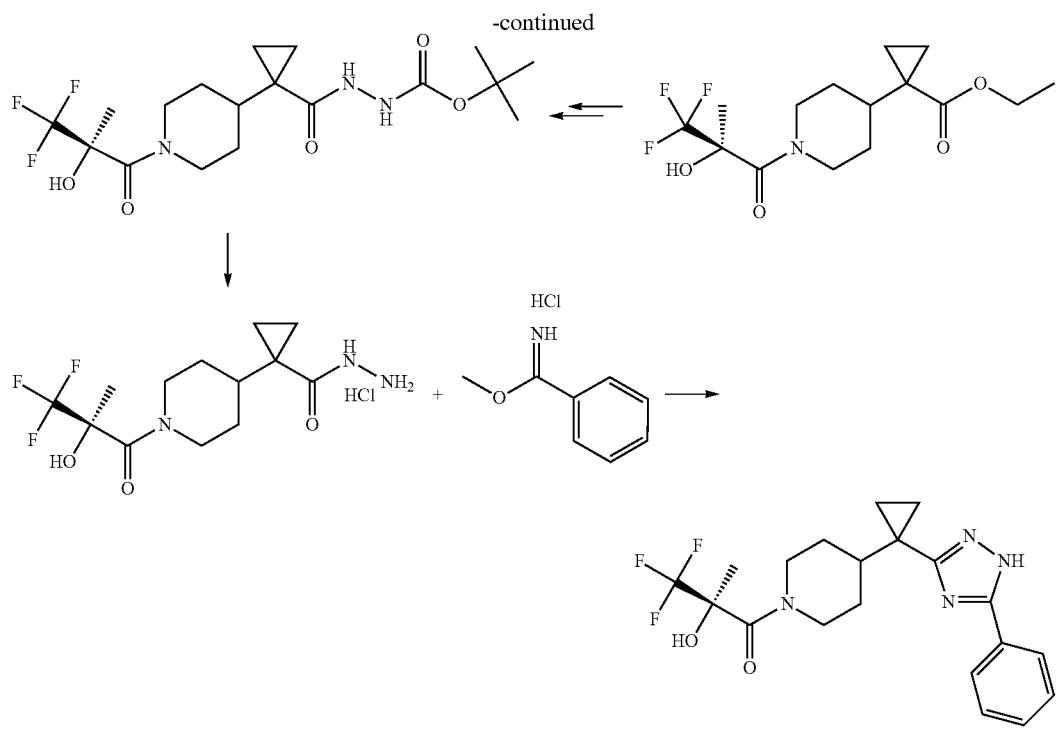

1.1 1-Pyridin-4-yl-cyclopropanecarboxylic acid ethyl ester

Pyridin-4-yl-acetic acid ethyl ester (2.00 g; 12.107 mmol) was dissolved in DMF (30.0 mL), lithium bis(trimethylsilyl) amide (1 M in THF; 18.16 mL; 18.161 mmol) was added and the mixture was stirred at 25 twice for 30 min. 1,2-Dibromoethane (1.25 mL; 14.529 mmol) was added and the mixture was stirred at 25° C. for 1 h. Lithium bis(trimethylsilyl)amide (1 M in THF; 18.16 mL; 18.161 mmol was added and the mixture stirred for another 1 h. The mixture was quenched under ice cooling with acetic acid (4 ml) and evaporated. The residue was partitioned between NH$_4$Cl solution and dichloromethane. The organic phase was separated and the water layer extracted twice with dichloromethane. The combined organic phases were dried over MgSO$_4$ and evaporated under reduced pressure. The residue was purified by RP-flash chromatography (Isco Companion). Yield: 1.90 g (82%) brown solid; HPLC/MS, Rt: 0.94 min; (M+H) 192.1; $^1$H NMR (400 MHz, DMSO-d$_6$/TFA) δ 8.96-8.84 (m, 2H), 8.17-8.08 (m, 2H), 4.14 (q, J=7.1 Hz, 1H), 1.81-1.77 (m, 1H), 1.56-1.48 (m, 1H), 1.17 (t, J=7.1 Hz, 3H).

1.2 1-Piperidin-4-yl-cyclopropanecarboxylic acid ethyl ester hydrochloride

Compound 1.1 (3.39 g; 17.728 mmol) was dissolved in ethanol (200.0 mL) and concentrated HCl (1.92 mL; 19.500 mmol) and hydrogenated over Platin(IV)-oxid hydrate at room temperature and normal pressure for 14 h. The reaction mixture was filtered and evaporated under reduced pressure. Yield: 4.14 g (100%) colorless solid; HPLC/MS, Rt: 0.34 min; (M+H) 198.2.

1.3 1-[1-((R)-3,3,3-Trifluoro-2-hydroxy-2-methyl-propionyl)-piperidin-4-yl]-cyclopropanecarboxylic acid ethyl ester Compound 1.2 (1.75 g; 7.487 mmol), (R)-3,3,3-trifluoro-2-hydroxy-2-methyl-propionic acid (1.21 g; 7.487 mmol) and [dimethylamino-([1,2,3]triazolo[4,5-b]pyridin-3-yloxy)-methylene]-dimethyl-ammonium hexafluoro phosphate (2.93 g; 7.487 mmol) were dissolved in dry DMF (40.0 mL). N-Ethyldiisopropylamine (5.14 mL; 29.948 mmol) was added and the mixture was stirred at room temperature for 5 h. The mixture was evaporated to dryness and the residue purified by RP-flash chromatography (CombiFlash RF 200). Yield: 2.53 g (100%) brown oil; HPLC/MS, Rt: 2.15 min; (M+H) 338.2.

1.4 1-[1-((R)-3,3,3-Trifluoro-2-hydroxy-2-methyl-propionyl)-piperidin-4-yl]-cyclopropanecarboxylic acid Compound 1.3 (2.53 g; 6.238 mmol) was dissolved in ethanol (50.0 mL) and sodium hydroxide solution (2 N; 50.0 mL) was added. The mixture was stirred at 25° C. for 2 d. The mixture was concentrated under reduced pressure, acidified with HCOOH to pH 4 and extracted three times with ethyl acetate. The combined organic layers were washed with brine, dried over Na$_2$SO$_4$, filtered and evaporated to dryness. Yield: 1.93 g (100%) orange oil; HPLC/MS, Rt: 1.72 min; (M+H) 310.1.

1.5 N'-{1-[1-((R)-3,3,3-Trifluoro-2-hydroxy-2-methyl-propionyl)-piperidin-4-yl]-cyclopropanecarbonyl}-hydrazinecarboxylic acid tert-butyl ester Compound 1.4 (1.10 g; 3.557 mmol) and (tert-butoxy) carbohydrazide (0.56 g; 4.268 mmol) were dissolved in dry DMF (5.0 mL) and the mixture was cooled in an ice bath.

[Dimethylamino-([1,2,3]triazolo[4,5-b]pyridin-3-yloxy)-methylene]-dimethyl-ammonium hexafluoro phosphate (1.76 g; 4.624 mmol) and subsequently N-ethyldiisopropylamine (1.82 mL; 10.670 mmol) were added, cooling was removed and the mixture was stirred for 20 h at 25° C.

The reaction mixture was evaporated and the residue subjected to RP-flash chromatography (Isco Companion). Yield: 1.10 g (73%) colourless solid; HPLC/MS, Rt: 1.78 min; (M+H-t-Bu) 368.1.

1.6 1-[1-((R)-3,3,3-Trifluoro-2-hydroxy-2-methyl-propionyl)-piperidin-4-yl]-cyclopropanecarboxylic acid hydrazide hydrochloride Compound 1.5 (1.10 g; 2.598 mmol) was dissolved in HCl solution (4.0 M in dioxane; 50.0 mL) and stirred at 25° C. for 20 h. The mixture was evaporated under reduced pressure. The residue was dissolved in acetonitrile (2 mL) and MTB-ether (50 mL) was added. The precipitate was collected by suction filtration and dried for 20 h at 25° C. Yield: 0.93 g (99%) off-white solid; HPLC/MS, Rt: 1.22 min; (M+H) 324.2.

1.7 (R)-3,3,3-Trifluoro-2-hydroxy-2-methyl-1-{4-[1-(5-phenyl-1H-[1,2,4]triazol-3-yl)-cyclopropyl]-piperidin-1-yl}-propan-1-one Compound 1.6 (100.0 mg; 0.278 mmol) and methyl benzenecarboxyimidate, hydrochloride (71.6 mg; 0.417 mmol) were dissolved in dry ethanol (2.0 mL) and N-ethyldiisopropylamine (0.25 mL; 1.470 mmol) was added. The mixture was heated to 80° C. and stirred at this temperature for 2 d. The reaction mixture was cooled to room temperature and evaporated under reduced pressure. The residue was purified using preparative HPLC. The combined fractions were lyophilized. Yield: 42.0 mg (37%) colourless solid; HPLC/MS, Rt: 1.87 min; (M+H) 409.2; $^1$H NMR (400 MHz, DMSO-d$_6$) δ 13.72 (s, br, 1H), 8.01-7.89 (m, 2H), 7.51-7.35 (m, 3H), 6.97 (s, 1H), 4.96-4.29 (m, 2H), 3.03-2.53 (m, 2H), 1.81-1.62 (m, 3H), 1.51 (s, 3H), 1.48-1.21 (m, 2H), 1.03-0.95 (m, 2H), 0.95-0.78 (m, 2H).

EXAMPLE 2

(R)-3,3,3-Trifluoro-1-{4-{1-[5-(4-fluorophenyl)-4H-[1,2,4]triazol-3-yl]-cyclopropyl}-piperidin-1-yl}-2-hydroxy-2-methyl-propan-1-one ("A2")

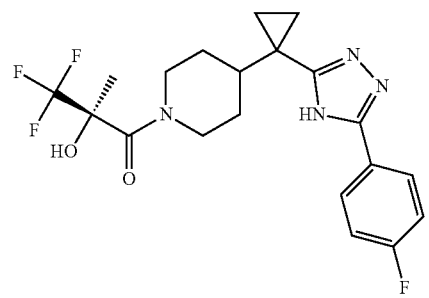 [SMILES: C[C@@](O)(C(=O)N1CCC(C2(c3nnc(-c4ccc(F)cc4)[nH]3)CC2)CC1)C(F)(F)F]

Preparation as described for example 1. Yield: 169 mg (36%) colorless solid; HPLC/MS, Rt: 1.99 min; (M+H) 427.1; $^1$H NMR (400 MHz, DMSO-d$_6$) δ 14.24-13.35 (m, 1H), 8.25-7.71 (m, 2H), 7.56-7.11 (m, 2H), 6.97 (s, 1H), 5.16-4.23 (m, 2H), 3.08-2.42 (m, 2H), 1.88-1.08 (m, 8H), 1.12-0.67 (m, 4H).

EXAMPLE 3

(R)-3,3,3-Trifluoro-2-hydroxy-2-methyl-1-{4-[1-methyl-1-(5-phenyl-4H-[1,2,4]triazol-3-yl)-ethyl]-piperidin-1-yl}-propan-1-one ("A3")

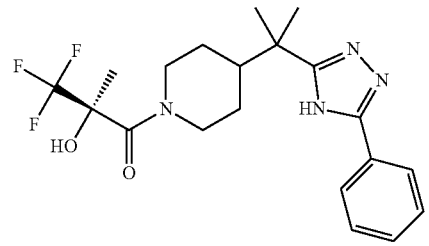 [SMILES: CC(C)(c1nnc(-c2ccccc2)[nH]1)C1CCN(C(=O)[C@@](C)(O)C(F)(F)F)CC1]

Reaction Scheme:

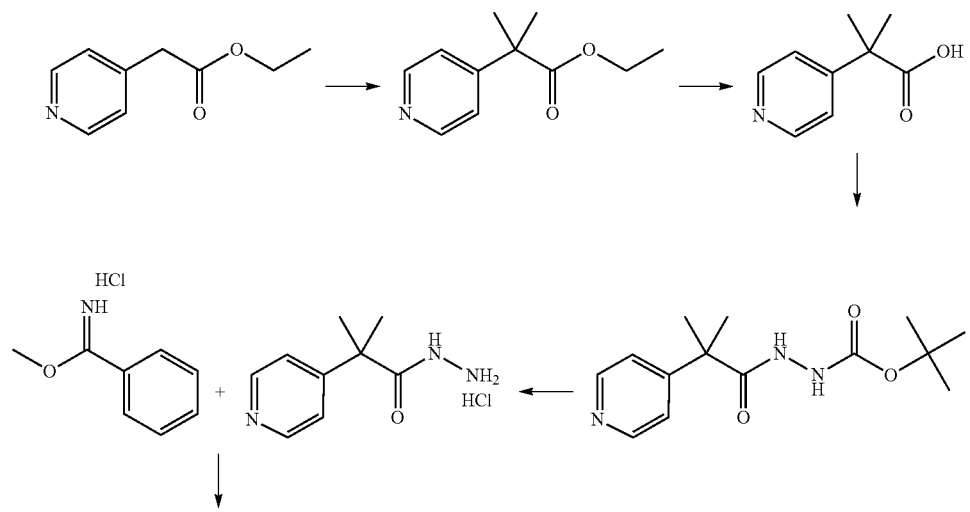

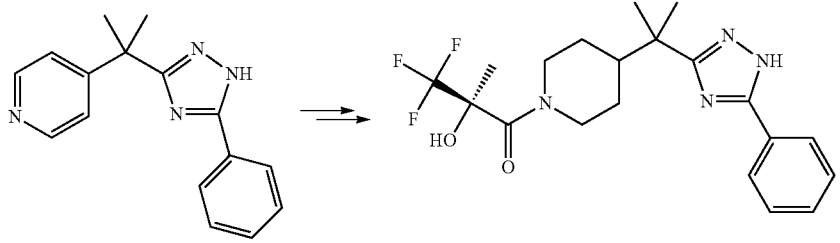

3.1 2-Methyl-2-pyridin-4-yl-propionic acid ethyl ester

Pyridin-4-yl-acetic acid ethyl ester (3.00 g; 17.616 mmol) was dissolved in dry DMF (40.0 mL) under nitrogen atmosphere, treated with lithium bis(trimethyl-silyl)amide (1 M in THF; 22.02 mL; 22.020 mmol) at room temperature and the mixture was stirred for 30 min. The reaction mixture was cooled in an ice bath, treated with iodomethane (1.68 mL; 26.424 mmol), gradually warmed to room temperature and stirred for 1 h. Further lithium bis(trimethylsilyl)amide (1 M in THF; 22.02 mL; 22.020 mmol) and dry DMF (15 mL) was added and the mixture stirred for 30 min after which another portion of iodomethane (1.68 mL; 26.424 mmol) was added under cooling. The resulting mixture was stirred at room temperature overnight. The reaction mixture was evaporated to dryness and the residue partitioned between ethyl acetate and water. The aqueous layer was extracted with ethyl acetate. The combined organic layers were washed with brine, dried over sodium sulfate, filtered and concentrated in vacuo. The residue was purified by flash chromatography (CombiFlashRF 200). Yield: 2.95 g (86%) colorless oil; HPLC/MS, Rt: 1.18 min; (M+H) 194.2

3.2 2-Methyl-2-pyridin-4-yl-propionic acid

Compound 3.1 (3.61 g; 18.663 mmol) was dissolved in ethanol (55.0 mL), sodium hydroxide solution (2 N; 50.0 mL) was added and the mixture was stirred at 20° C. for 20 h. Ethanol was removed by evaporation and the aqueous residue was neutralized under ice cooling using hydrochloric acid (pH~7). The mixture was concentrated to dryness, the colourless residue triturated three times with dichloromethane/methanol, and the combined filtrates were evaporated to dryness. Yield: 2.63 g (85%) colourless solid; HPLC/MS, Rt: 0.43 min; (M+H) 166.1.

3.3 N'-(2-Methyl-2-pyridin-4-yl-propionyl)-hydrazinecarboxylic acid tert-butyl ester Compound 3.2 (1.85 g; 11.199 mmol) and (tert-butoxy)carbohydrazide (1.64 g; 12.319 mmol) were dissolved in dry DMF (35.0 mL) and the mixture was cooled in an ice bath. [Dimethylamino-([1,2,3]triazolo[4,5-b]pyridin-3-yloxy)-methylene]-dimethyl-ammonium hexafluoro phosphate (5.05 g; 12.879 mmol) and N-ethyldiisopropylamine (5.83 mL; 33.598 mmol) were added, cooling was removed and the mixture was stirred at room temperature for 2 h. The reaction mixture was evaporated to dryness and the residue purified by RP-flash chromatography (CombiFlashRF 200). Yield: 2.74 g (88%) light yellow oil; HPLC/MS, Rt: 0.34/1.04 min; (M+H) 280.2.

3.4 2-Methyl-2-pyridin-4-yl-propionic acid hydrazide hydrochloride

HCl solution (1N, 16.0 mL) was added to compound 3.3 (2.09 g; 7.482 mmol) and the mixture stirred at room temperature. After 10 min a colorless suspension was formed which was stirred over night at ambient temperature. The reaction mixture was lyophilisated and the product used in the next step without further purification.

3.5 4-[1-Methyl-1-(5-phenyl-1H-[1,2,4]triazol-3-yl)-ethyl]-pyridine

Compound 3.4 (744.0 mg; 3.450 mmol) and methyl benzimidate hydrochloride (888.0 mg; 5.174 mmol) were dissolved in ethanol (14.0 mL). N-Ethyldiisopropylamine (1.76 mL; 10.349 mmol) was added and the mixture was heated to 80° C. overnight. The reaction was cooled to room temperature and concentrated in vacuo. The residue purified by flash chromatography (CombiFlashRF 200). Yield: 657 mg (72%) colourless solid; HPLC/MS, Rt: 1.23 min; (M+H)

3.6 4-[1-Methyl-1-(5-phenyl-4H-[1,2,4]triazol-3-yl)-ethyl]-piperidine hydrochloride Compound 3.5 (485.0 mg; 1.835 mmol) was dissolved in ethanol (10.0 mL) and conc. HCl (0.34 mL; 3.511 mmol) and hydrogenated over Pd—C(5%) at room temperature and normal pressure for 48 h. The reaction mixture was filtered and evaporated under reduced pressure. Yield: 532 mg (94%) yellow oil; HPLC/MS, Rt: 1.25 min; (M+H) 271.2.

3.7 (R)-3,3,3-Trifluoro-2-hydroxy-2-methyl-1-{4-[1-methyl-1-(5-phenyl-4H-[1,2,4]triazol-3-yl)-ethyl]-piperidin-1-yl}-propan-1-one (R)-3,3,3-Trifluoro-2-hydroxy-2-methylpropionic acid (255.0 mg; 1.612 mmol) was dissolved in dichloromethane (10.0 mL). 1-Chloro-N,N,2-trimethyl-1-propenylamine (213 μl; 1.612 mmol) was added and the colorless solution was stirred at room temperature for 90 min. This solution was slowly added to a solution of compound 3.6 (430.0 mg; 1.401 mmol) and triethylamine (583 μl; 4.204 mmol) in dichloromethane (10.0 ml) and the reaction mixture was stirred at room temperature for 90 min. The reaction mixture was diluted with water and saturated aqueous NaHCO$_3$-solution and extracted with dichloromethane. The combined organic layers were dried over sodium sulfate, filtered and concentrated in vacuo. The residue was purified by RP-flash chromatography (CombiFlashRF 200) and freeze-dried. Yield: 118 mg (20%) colorless solid; HPLC/MS, Rt: 1.98 min; (M+H) 411.2; $^1$H NMR (400 MHz, DMSO-d$_6$) δ 14.1-13.46 (m, 1H), 8.05-7.92 (m, 2H), 7.58-7.32 (m, 3H), 6.96 (s, 1H), 4.91-4.28 (m, 2H), 3.03-2.70 (m, 1H), 1.95-1.79 (m, 1H), 1.61-1.42 (m, 5H), 1.32 (s, 6H), 1.28-0.96 (m, 3H).

EXAMPLE 4

(R)-1-{4-[1-(5-Cyclohexyl-4H-[1,2,4]triazol-3-yl)-1-methyl-ethyl]-piperidin-1-yl}-3,3,3-trifluoro-2-hydroxy-2-methyl-propan-1-one ("A4")

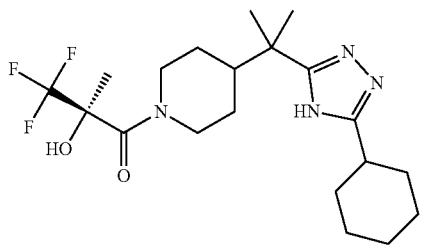 [SMILES: CC(C)(c1nnc(C2CCCCC2)[nH]1)C1CCN(C(=O)[C@@](C)(O)C(F)(F)F)CC1]

Reaction Scheme:

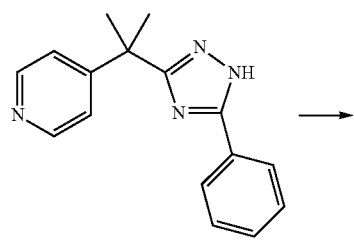

↓

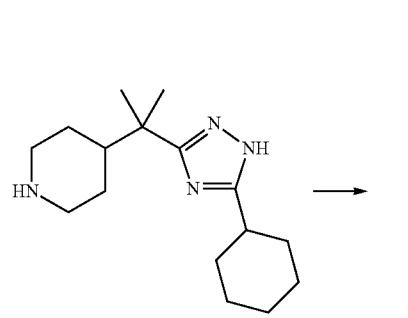

↓

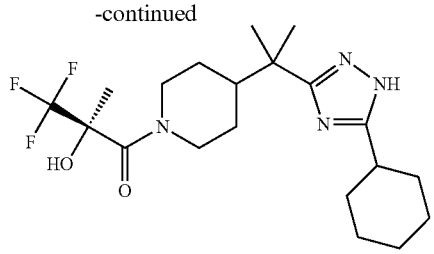

4.1 4-[1-(5-Cyclohexyl-4H-[1,2,4]triazol-3-yl)-1-methyl-ethyl]-piperidine

Compound 3.5 (97.0 mg; 0.367 mmol) was dissolved in ethanol (10.0 mL) and hydrogenated over Platin(IV)-oxid hydrate at room temperature and normal pressure for 35 h. The reaction mixture was filtered and evaporated under reduced pressure. Yield: 98 mg (97%) red-brown oil; HPLC/MS, Rt: 1.28 min; (M+H) 277.4.

4.2 (R)-1-{4-[1-(5-Cyclohexyl-4H-[1,2,4]triazol-3-yl)-1-methyl-ethyl]-piperidin-1-yl}-3,3,3-trifluoro-2-hydroxy-2-methyl-propan-1-one Preparation as described for example 3 (step 3.7). Yield: 3 mg (2%) colorless solid; HPLC/MS, Rt: 1.78 min; (M+H) 417.3.

EXAMPLE 5

(R)-3,3,3-Trifluoro-2-hydroxy-2-methyl-1-{4-[1-(5-phenyl-[1,3,4]oxadiazol-2-yl)-cyclopropyl]-piperidin-1-yl}-propan-1-one ("A5")

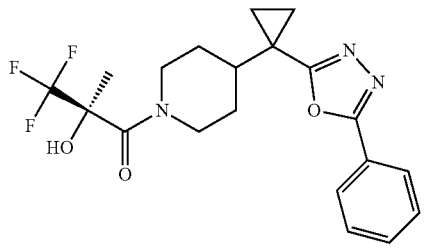 [SMILES: C[C@@](O)(C(=O)N1CCC(C2(c3nnc(-c4ccccc4)o3)CC2)CC1)C(F)(F)F]

Reaction Scheme:

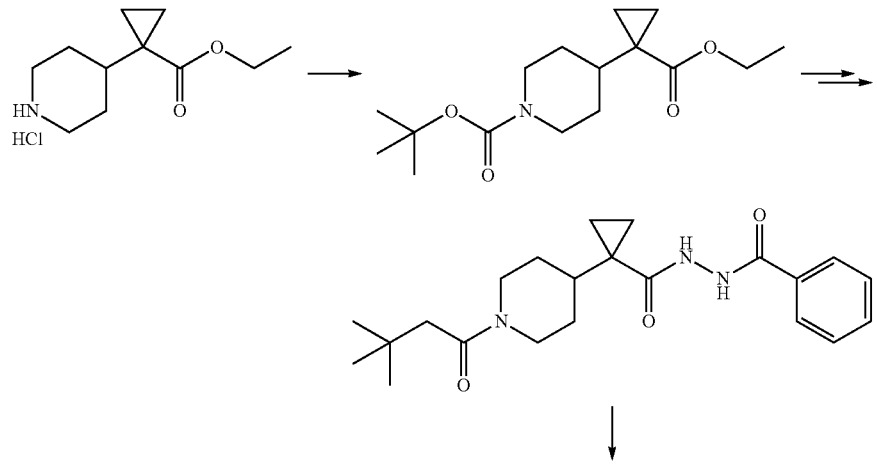

↓

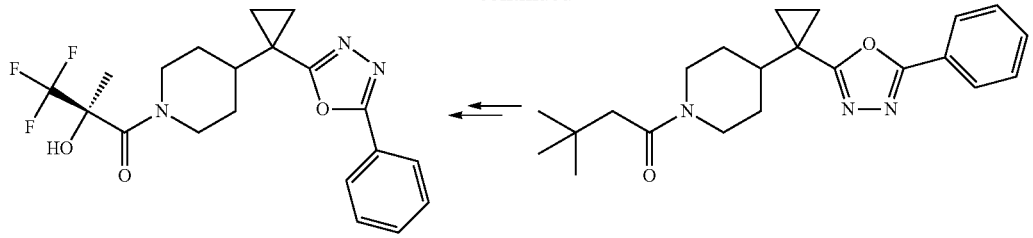

5.1 4-(1-Ethoxycarbonyl-cyclopropyl)-piperidine-1-carboxylic acid tert-butyl ester To a solution of compound 1.2 (4.14 g; 17.712 mmol) in water (60.0 mL) sodium bicarbonate (4.51 g; 53.137 mmol) and di-tert-butyldicarbonate (3.83 mL; 17.712 mmol), dissolved in 1,4-dioxane (110.0 mL), were added and the mixture stirred for 2 h at room temperature. The suspension was concentrated under reduced pressure, diluted with water (60 mL) and extracted with ethyl acetate. The combined organic layers were washed with brine, dried over sodium sulfate, filtered, and concentrated in vacuo. The residue was purified by flash chromatography (CombiFlashRF 200). Yield: 3.92 g (74%) colorless solid; HPLC/MS, Rt: 2.57 min; (M+H-BOC) 198.2.

5.2 4-(1-Carboxy-cyclopropyl)-piperidine-1-carboxylic acid tert-butyl ester

Compound 5.1 (3.46 g; 11.630 mmol) was dissolved in ethanol (75.0 mL), treated with sodium hydroxide solution (2 N; 75.0 ml; 150.000 mmol) and the solution stirred for 4 d. The mixture was concentrated under reduced pressure, acidified with formic acid (~pH4) and extracted with ethyl acetate. The combined organic phases were dried over MgSO4 and evaporated under reduced pressure. Yield: 3.12 g (100%) yellow solid; used in the next step without further purification.

5.3 4-[1-(N'-Benzoyl-hydrazinocarbonyl)-cyclopropyl]-piperidine-1-carboxylic acid tert-butyl ester Compound 5.2 (433.2 mg; 1.608 mmol) and benzoic acid hydrazide (210.0 mg; 1.608 mmol) were dissolved in dry DMF (6.00 ml; 47,978 äq.). [Dimethylamino-([1,2,3]triazolo[4,5-b]pyridin-3-yloxy)-methylene]-dimethyl-ammonium hexafluoro phosphate (HATU) (703.2 mg; 1.849 mmol) and subsequently N-ethyldiisopropylamine (0.82 mL; 4.825 mmol) were added and the yellow solution was stirred at room temperature for 1 d. The reaction mixture was evaporated to dryness and the residue purified by RP-flash chromatography (CombiFlashRF 200).

Yield: 318 mg (51%) light yellow solid; HPLC/MS, Rt: 1.97 min; (M+H) 288.2.

5.4 4-[1-(5-Phenyl-[1,3,4]oxadiazol-2-yl)-cyclopropyl]-piperidine-1-carboxylic acid tert-butyl ester A mixture of compound 5.3 (114.8 mg; 0.296 mmol) and Burgess reagent (423.4 mg; 1.777 mmol) dissolved in dry THF (1.50 mL) was heated in a CEM microwave reactor for 20 min at 130° C. The reaction mixture was cooled to room temperature, diluted with water and extracted with ethyl acetate. The combined organic layers were washed with brine, dried over sodium sulfate, filtered, and concentrated in vacuo. The residue was purified by flash chromatography (CombiFlashRF 200). Yield: 108 mg (99%) yellow oil; HPLC/MS, Rt: 2.57 min; (M+H-t-Bu) 314.1.

5.5 4-[1-(5-Phenyl-[1,3,4]oxadiazol-2-yl)-cyclopropyl]-piperidine hydrochloride Hydrogen chloride solution (4.0 M in dioxane; 5.0 mL) was added to compound 5.4 (384.0 mg; 1.039 mmol), dissolved in dioxane (5.0 mL), and stirred for 14 h at ambient temperature. The reaction was concentrated in vacuo and the residue used in the next step without further purification. Yield: 317 mg (100%) beige solid.

5.6 (R)-3,3,3-Trifluoro-2-hydroxy-2-methyl-1-{4-[1-(5-phenyl-[1,3,4]oxadiazol-2-yl)-cyclopropyl]-piperidin-1-yl}-propan-1-one Compound 5.5 (127.0 mg; 0.415 mmol), (R)-3,3,3-trifluoro-2-hydroxy-2-methyl-propionic acid (65.6 mg; 0.415 mmol) and [dimethylamino-([1,2,3]triazolo[4,5-b]pyridin-3-yloxy)-methylene]-dimethyl-ammonium hexafluoro phosphate (HATU) (157.9 mg; 0.415 mmol) were dissolved in dry DMF (5.0 mL) and N-ethyldiisopropylamine (283.0 μL; 1.665 mmol) was added. The reaction mixture was stirred at room temperature for 6 h. The mixture was evaporated to dryness and the residue purified by RP-flash chromatography (CombiFlashRF 200). Yield: 149 mg (87%) colorless solid; HPLC/MS, Rt: 2.19 min; (M+H) 410.2; ¹H NMR (400 MHz, DMSO-d₆) δ 7.97-7.91 (m, 2H), 7.64-7.54 (m, 3H), 7.01 (s, 1H), 4.89-4.40 (m, 2H), 3.06-2.81 (m, 1H), 2.65-2.50 (m, 1H), 1.85-1.67 (m, 3H), 1.64-1.39 (m, 5H), 1.28-1.21 (m, 2H), 1.12-1.03 (m, 2H).

EXAMPLE 6

(R)-3,3,3-Trifluoro-1-{4-{1-[5-(4-fluoro-phenyl)-[1,3,4]oxadiazol-2-yl]-cyclopropyl}-piperidin-1-yl}-2-hydroxy-2-methyl-propan-1-one ("A6")

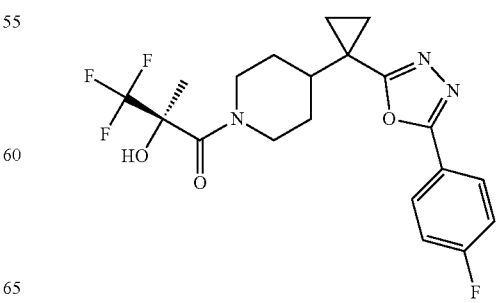

Preparation as described for example 5. Yield: 166 mg (59%) colorless solid; HPLC/MS, Rt: 2.23 min; (M+H) 428.2; $^1$H NMR (400 MHz, DMSO-$d_6$) δ 8.04-7.97 (m, 2H), 7.46-7.38 (m, 2H), 7.01 (s, 1H), 4.93-4.35 (m, 2H), 3.06-2.83 (m, 1H), 2.64-2.44 (m, 1H), 1.84-1.67 (m, 2H), 1.64-1.38 (m, 6H), 1.29-1.19 (m, 2H), 1.13-1.02 (m, 2H).

The following compounds were prepared analogously:

EXAMPLE 7

(R)-3,3,3-Trifluoro-2-hydroxy-2-methyl-1-{4-[1-(5-methyl-[1,3,4]oxadiazol-2-yl)-cyclopropyl]-piperidin-1-yl}-propan-1-one ("A7")

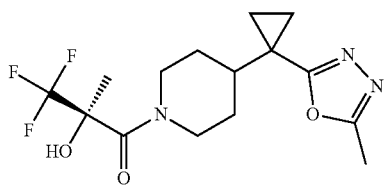 [SMILES: Cc1nnc(C2(C3CCN(C(=O)[C@@](C)(O)C(F)(F)F)CC3)CC2)o1]

Yield: 114 mg (52%) colorless solid; HPLC/MS, Rt: 1.73 min; (M+H) 348.1; $^1$H NMR (400 MHz, DMSO-$d_6$) δ 6.99 (s, 1H), 5.27-3.99 (m, 4H), 3.06-2.70 (m, 1H), 2.41 (s, 3H), 1.79-1.31 (m, 7H), 1.15-0.45 (m, 4H).

EXAMPLE 8

(R)-1-{4-[1-(5-tert-Butyl-[1,3,4]oxadiazol-2-yl)-cyclopropyl]-piperidin-1-yl}-3,3,3-trifluoro-2-hydroxy-2-methyl-propan-1-one ("A8")

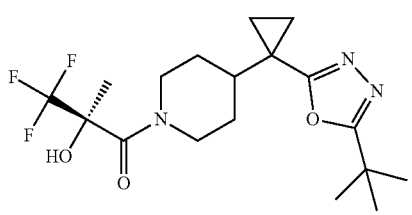 [SMILES: CC(C)(C)c1nnc(C2(C3CCN(C(=O)[C@@](C)(O)C(F)(F)F)CC3)CC2)o1]

Yield: 266 mg (93%) colorless solid; HPLC/MS, Rt: 2.12 min; (M+H) 390.2; $^1$H NMR (400 MHz, DMSO-$d_6$) δ 7.00 (s, 1H), 4.91-4.36 (m, 2H), 3.02-2.78 (m, 1H), 1.78-1.64 (m, 2H), 1.64-1.34 (m, 7H), 1.30 (s, 9H), 1.13-1.06 (m, 2H), 1.03-0.96 (m, 2H).

EXAMPLES 9 AND 10

Preparation of (R)-3,3,3-Trifluoro-2-hydroxy-2-methyl-1-{4-[1-methyl-1-(5-phenyl-[1,3,4]oxadiazol-2-yl)-ethyl]-piperidin-1-yl}-propan-1-one ("A9")

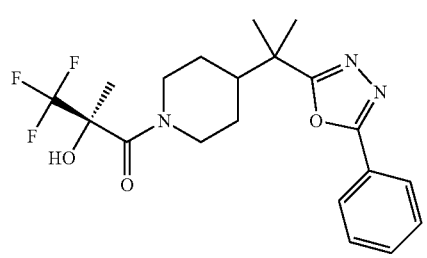 [SMILES: CC(C)(c1nnc(-c2ccccc2)o1)C1CCN(C(=O)[C@@](C)(O)C(F)(F)F)CC1]

And (R)-1-{4-[1-(5-Cyclohexyl-[1,3,4]oxadiazol-2-yl)-1-methyl-ethyl]-piperidin-1-yl}-3,3,3-trifluoro-2-hydroxy-2-methyl-propan-1-one ("A10")

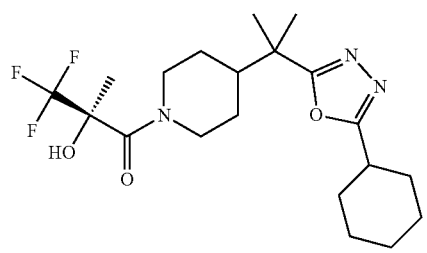 [SMILES: CC(C)(c1nnc(C2CCCCC2)o1)C1CCN(C(=O)[C@@](C)(O)C(F)(F)F)CC1]

Reaction Scheme:

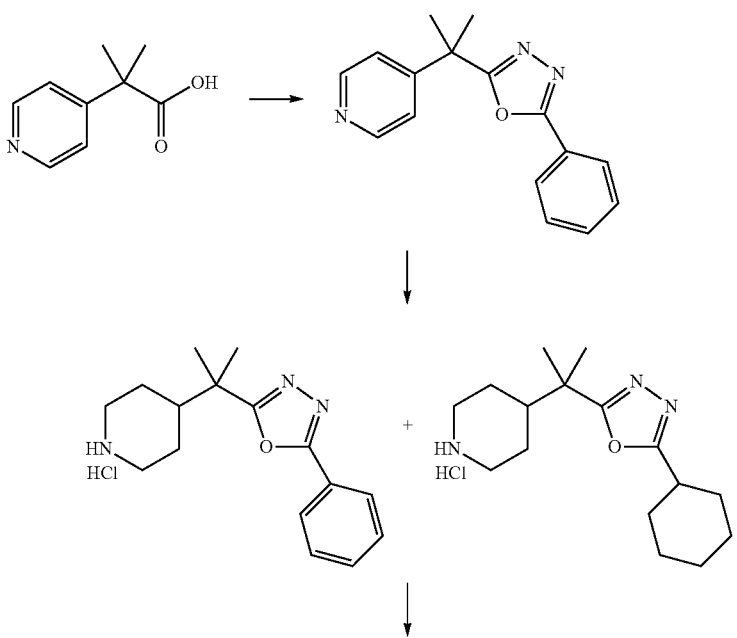

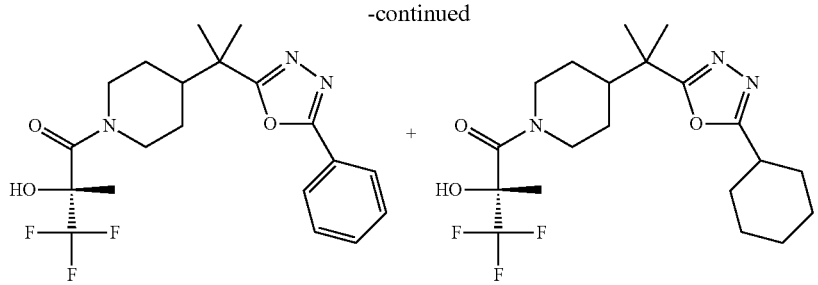

9.1 4-[1-Methyl-1-(5-phenyl-[1,3,4]oxadiazol-2-yl)-ethyl]-pyridine

Compound 3.2 (500.0 mg; 3.027 mmol), benzohydrazide (412.1 mg; 3.027 mmol) and 2-chloro-4,5-dihydro-1,3-dimethyl-1H-imidazolium chloride (511.7 mg; 3.027 mmol) were suspended in dichloromethane (20.0 mL). Triethylamine (1.70 mL; 12.107 mmol) was added and the reaction mixture stirred at room temperature for 14 h. Further 2-chloro-4,5-dihydro-1,3-dimethyl-1H-imidazolium chloride (511.7 mg; 3.027 mmol) and triethylamine (848 µl; 6.054 mmol) was added and the reaction was stirred at room temperature for 48 h. The reaction mixture was diluted with saturated aqueous NaHCO$_3$-solution and extracted with dichloromethane. The combined organic layers were dried over sodium sulfate, filtered, and concentrated in vacuo. The residue was purified by flash chromatography (CombiFlashRF 200). Yield: 130 mg (16%) orange oil; HPLC/MS, Rt: 1.48 min; (M+H) 266.1.

9.2 4-[1-Methyl-1-(5-phenyl-[1,3,4]oxadiazol-2-yl)-ethyl]-piperidine hydrochloride and 4-[1-(5-Cyclohexyl-[1,3,4]oxadiazol-2-yl)-1-methyl-ethyl]-piperidine hydrochloride Compound 9.1 (120.0 mg; 0.452 mmol) was dissolved in ethanol (10.0 mL) and 1 M HCl (0.5 mL; 0.5 mmol) and hydrogenated over platin(IV)-oxid hydrate at room temperature and normal pressure for 2 h. The reaction mixture was filtered and evaporated under reduced pressure. The residue, which contained approximately a 1/1 mixture of the title compounds, was used in the next step without further purification.

9.3 (R)-3,3,3-Trifluoro-2-hydroxy-2-methyl-1-{4-[1-methyl-1-(5-phenyl-[1,3,4]oxadiazol-2-yl)-ethyl]-piperidin-1-yl}-propan-1-one and (R)-1-{4-[1-(5-Cyclohexyl-[1,3,4]oxadiazol-2-yl)-1-methyl-ethyl]-piperidin-1-yl}-3,3,3-trifluoro-2-hydroxy-2-methyl-propan-1-one Preparation and work-up as described for example 3 (step 3.7). The compounds were separated by preparative HPLC. The combined fractions were evaporated to dryness. The residue was dissolved in acetonitrile, diluted with water and lyophilized.

"A9": 31 mg (33%) colorless solid; LC/MS, Rt: 2.19 min; (M+H) 412.2; $^1$H NMR (500 MHz, DMSO-d$_6$) δ 8.02-7.97 (m, 2H), 7.65-7.57 (m, 3H), 6.98 (s, 1H), 4.87-4.68 (m, 1H), 4.54-4.36 (m, 1H), 3.01-2.81 (m, 1H), 2.59-2.45 (m, 1H), 1.99-1.90 (m, 1H), 1.66-1.55 (m, 2H), 1.48 (s, 3H), 1.39 (s, 6H), 1.32-1.06 (m, 2H).

"A10": 48 mg (51%) colorless solid; LC/MS, Rt: 2.31 min; (M+H) 418.2; $^1$H NMR (400 MHz, DMSO-d$_6$) δ 7.00 (s, 1H), 4.86-4.65 (m, 1H), 4.54-4.33 (m, 1H), 2.96-2.79 (m, 2H), 2.01-1.92 (m, 2H), 1.87-1.76 (m, 1H), 1.75-1.67 (m, 2H), 1.67-1.59 (m, 1H), 1.58-1.44 (m, 7H), 1.43-1.34 (m, 2H), 1.34-0.98 (m, 10H).

EXAMPLE 11

(R)-3,3,3-Trifluoro-2-hydroxy-2-methyl-1-{3-methyl-4-[1-(5-phenyl-1H-[1,2,4]triazol-3-yl)-cyclopropyl]-piperidin-1-yl}-propan-1-one, Mixture of Diastereomers ("A11")

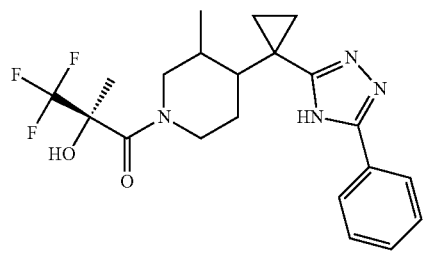

Reaction Scheme:

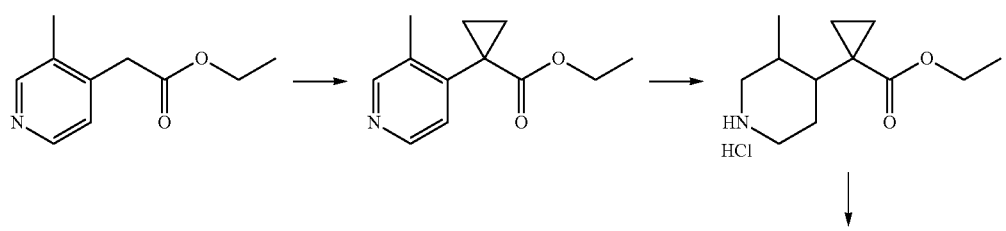

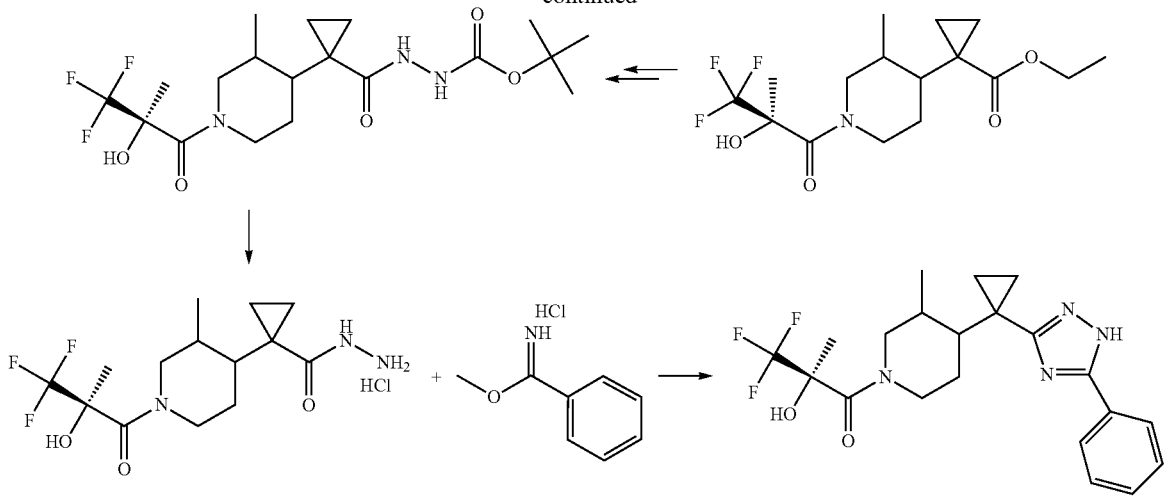

11.1 (3-Methyl-pyridin-4-yl)-acetic acid ethyl ester 3,4-Dimethylpyridine (2.30 mL; 20.499 mmol) was dissolved in THF (10.0 mL), lithium bis(trimethylsilyl)amide (20% solution in THF; 61.50 mL; 61.496 mmol) was added at room temperature under nitrogen atmosphere and the mixture was stirred for 30 min. Diethyl carbonate (3.23 mL; 26,648 mmol) was added and the mixture was stirred at room temperature for 1 h. A saturated solution of NH$_4$Cl (50 mL) was added and the aqueous mixture was extracted with diethyl ether. The combined organic phases were dried over sodium sulfate, filtered, and evaporated to dryness. The residue was purified by RP-flash chromatography (Isco Companion). Yield: 1.40 g (38%) yellow oil; Rt: 1.44 min; (M+H) 180.1.

11.2 1-(3-Methyl-pyridin-4-yl)-cyclopropanecarboxylic acid ethyl ester

Compound 11.1 (1.40 g; 7.810) was dissolved in dry DMF (10.0 mL), lithium bis(trimethylsilyl)amide (1 M in THF; 9.37 mL; 9.370 mmol) was added at room temperature and the mixture was stirred for 30 min. 1,2-Dibromoethane (942.5 µl; 10.940 mmol) was added and the mixture was stirred at room temperature for 1 h. Further lithium bis(trimethylsilyl)amide (1 M in THF; 9.37 mL; 9.370 mmol) was added and the mixture stirred for 1 h. The mixture was quenched under ice cooling with acetic acid (4 mL) and evaporated to dryness. The residue was partitioned between NH$_4$Cl solution and dichloromethane. The organic phase was separated and the water phase extracted with dichloromethane. The combined organic phases were dried over MgSO$_4$, filtered and evaporated under reduced pressure. The residue was purified by RP-flash chromatography (Isco Companion). Yield: 590 mg (37%) yellow oil; Rt: 1.63 min; (M+H) 206.1.

11.3 1-(3-Methyl-piperidin-4-yl)-cyclopropanecarboxylic acid ethyl ester hydrochloride Hydrogenation of compound 11.2 (590.0 g; 2.875 mmol) was performed and worked-up as described for compound 1.2. Yield: 676 mg (95%) oil. The product was used in the next step without further purification.

11.4 1-[3-Methyl-1-((R)-3,3,3-trifluoro-2-hydroxy-2-methyl-propionyl)-piperidin-4-yl]-cyclopropanecarboxylic acid ethyl ester Acylation of compound 11.3 (676.0 mg; 2.728 mmol) was performed as described for compound 1.3. The crude product was purified by RP-flash chromatography. Yield: 727 mg (76%) oil; Rt: 2.18 min; (M+H) 352.2.

11.5 1-[3-Methyl-1-((R)-3,3,3-trifluoro-2-hydroxy-2-methyl-propionyl)-piperidin-4-yl]-cyclopropanecarboxylic acid Compound 11.4 (727.0 mg; 1.721 mmol) was saponified as described for compound 1.3. Yield: 510 mg (92%) oil; Rt: 1.71 min; (M+H) 324.2. The product was used in the next step without further purification.

11.6 N'-{1-[3-Methyl-1-((R)-3,3,3-trifluoro-2-hydroxy-2-methyl-propionyl)-piperidin-4-yl]-cyclopropanecarbonyl}-hydrazinecarboxylic acid tert-butyl ester Preparation of the title compound using compound 11.5 (510.0 mg; 1.577 mmol) was performed as described for compound 1.5 and purified by RP-flash chromatography (Isco Companion). Yield: 402 mg (58%) solid; Rt: 1.79 min; (M+H-t-Bu) 382.2.

11.7 1-[3-Methyl-1-((R)-3,3,3-trifluoro-2-hydroxy-2-methyl-propionyl)-piperidin-4-yl]-cyclopropanecarboxylic acid hydrazide hydrochloride Boc-cleavage was performed with compound 11.6 (402.0 mg; 0.919 mmol) as described for compound 1.5 (step 1.6). Yield: 343 mg (100%) oil; Rt: 1.27 min; (M+H) 382.2. The product was used in the next step without further purification.

11.8 (R)-3,3,3-Trifluoro-2-hydroxy-2-methyl-1-{3-methyl-4-[1-(5-phenyl-4H-[1,2,4]triazol-3-yl)-cyclopropyl]-piperidin-1-yl}-propan-1-one Compound 11.7 (306 mg; 0.819 mmol) and methyl benzenecarboxyimidate hydrochloride (215.0 mg; 1.228 mmol) were dissolved in dry ethanol (3.3 mL). N-Ethyldiisopropylamine (0.42 mL; 2.456 mmol) was added and the mixture was heated at 85° C. for 15 h. The reaction was concentrated under reduced pressure and the residue purified by RP-flash chromatography (CombiFlashRF 200). Yield: 81 mg (23%) colorless solid; Rt: 1.99 min; (M+H) 423.2.

EXAMPLE 12

(R)-3,3,3-Trifluoro-2-hydroxy-2-methyl-1-{3-methyl-4-[1-(5-phenyl-[1,3,4]oxadiazol-2-yl)-cyclopropyl]-piperidin-1-yl}-propan-1-one, Mixture of Diastereomers ("A12")

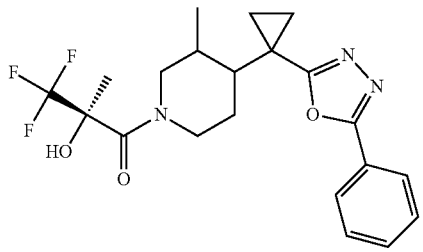

Reaction Scheme:

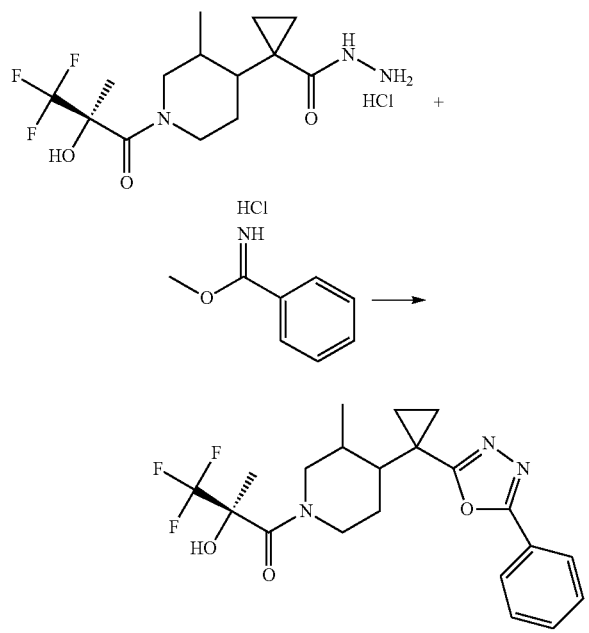

Compound 11.7 (343.0 mg; 0.918 mmol) and methyl benzenecarboxyimidate hydrochloride (236.2 mg; 1.376 mmol) were dissolved in dry ethanol (2.0 mL). N-Ethyldiisopropylamine (0.31 mL; 1.835 mmol) was added, the mixture was heated to 80° C. and stirred at this temperature for 44 h. The reaction was cooled to room temperature and evaporated under reduced pressure. The residue was purified by preparative HPLC. Yield: 152 mg (39%) solid; 2.20 min; (M+H) 424.2.

EXAMPLES 13 AND 14

Preparation of (R)-3,3,3-Trifluoro-2-hydroxy-2-methyl-1-{(3R,4R)-3-methyl-4-[1-(5-phenyl-4H-[1,2,4]triazol-3-yl)-cyclopropyl]-piperidin-1-yl}-propan-1-one ("A13")

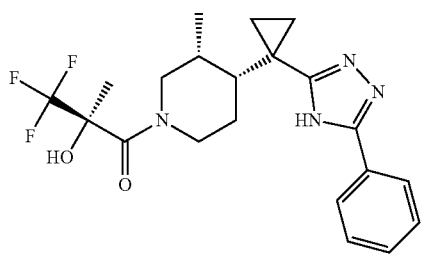 [SMILES: C[C@H]1CN(C(=O)[C@@](C)(O)C(F)(F)F)CC[C@H]1C1(c2nnc(-c3ccccc3)[nH]2)CC1]

And (R)-3,3,3-Trifluoro-2-hydroxy-2-methyl-1-{(3S,4S)-3-methyl-4-[1-(5-phenyl-4H-[1,2,4]triazol-3-yl)-cyclopropyl]-piperidin-1-yl}-propan-1-one ("A14")

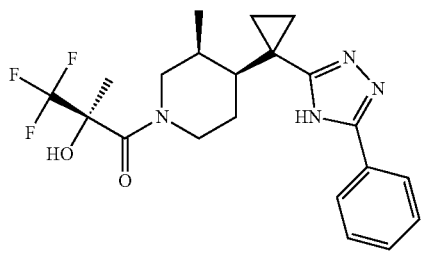 [SMILES: C[C@@H]1CN(C(=O)[C@@](C)(O)C(F)(F)F)CC[C@@H]1C1(c2nnc(-c3ccccc3)[nH]2)CC1]

The preparative separation of the diastereomers of example 11 was performed by SFC (column: ChiralPak AD-H; eluent: $CO_2$:methanol—85:15). The combined fractions were evaporated to dryness. The oily residue was dissolved in acetonitrile, diluted with water and lyophilized.

"A13": 29.5 mg colorless solid; LC/MS, Rt: 2.00 min; (M+H) 423.1; $^1$H NMR (400 MHz, DMSO-$d_6$, 90° C.) δ 13.54 (s, 1H), 8.04-7.87 (m, 2H), 7.56-7.32 (m, 3H), 6.66 (s, 1H), 4.81-4.63 (m, 1H), 4.44-4.24 (m, 1H), 2.98-2.76 (m, 2H), 2.44-2.36 (m, 1H), 2.16-2.01 (m, 1H), 1.65-1.49 (m, 4H), 1.49-1.36 (m, 1H), 1.31-1.17 (m, 1H), 1.00-0.88 (m, 2H), 0.83 (d, J=7.0 Hz, 3H), 0.75-0.67 (m, 1H).

"A14": 26 mg colorless solid; LC/MS, Rt: 1.99 min; (M+H) 423.2; $^1$H NMR (400 MHz, DMSO-$d_6$, 90° C.) δ 13.52 (s, 1H), 8.04-7.87 (m, 2H), 7.55-7.32 (m, 3H), 6.65 (s, 1H), 4.80-4.63 (m, 1H), 4.44-4.30 (m, 1H), 2.96-2.77 (m, 2H), 2.43-2.28 (m, 1H), 2.17-1.93 (m, 1H), 1.67-1.46 (m, 4H), 1.46-1.34 (m, 1H), 1.34-1.13 (m, 1H), 1.06-0.86 (m, 2H), 0.82 (d, J=7.0 Hz, 3H), 0.76-0.58 (m, 1H).

EXAMPLES 15 AND 16

Preparation of (R)-3,3,3-Trifluoro-2-hydroxy-2-methyl-1-{(S)-3-methyl-4-[1-(5-phenyl-[1,3,4]oxadiazol-2-yl)-cyclopropyl]-piperidin-1-yl}-propan-1-one ("A15")

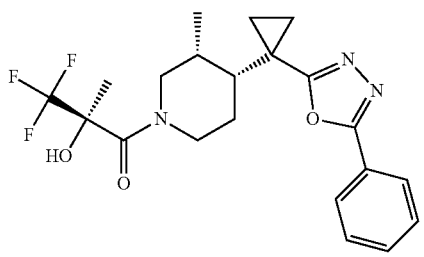 [SMILES: C[C@H]1CN(C(=O)[C@@](C)(O)C(F)(F)F)CC[C@H]1C1(c2nnc(-c3ccccc3)o2)CC1]

And (R)-3,3,3-Trifluoro-2-hydroxy-2-methyl-1-{(R)-3-methyl-4-[1-(5-phenyl-[1,3,4]oxadiazol-2-yl)-cyclopropyl]-piperidin-1-yl}-propan-1-one ("A16")

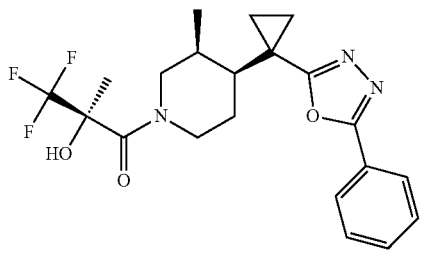 [SMILES: C[C@@H]1CN(C(=O)[C@@](C)(O)C(F)(F)F)CC[C@@H]1C1(c2nnc(-c3ccccc3)o2)CC1]

The preparative separation of the diastereomers of example 12 was performed by SFC (column: ChiralPak AD-H; eluent: CO$_2$:methanol—86:14). The combined fractions were evaporated to dryness. The oily residue was dissolved in acetonitrile, diluted with water and lyophilized.

"A15": 58 mg colorless solid; LC/MS, Rt: 2.21 min; (M+H) 424.1; $^1$H NMR (400 MHz, DMSO-d$_6$, 90° C.) δ 8.00-7.92 (m, 2H), 7.64-7.53 (m, 3H), 6.68 (s, 1H), 4.79-4.69 (m, 1H), 4.41-4.32 (m, 1H), 2.96-2.82 (m, 2H), 2.29-2.22 (m, 1H), 2.22-2.13 (m, 1H), 1.75-1.62 (m, 1H), 1.56 (s, 3H), 1.54-1.47 (m, 1H), 1.34-1.25 (m, 1H), 1.16-1.05 (m, 3H), 0.83 (d, J=7.0 Hz, 3H).

"A16": 62 mg colorless solid; LC/MS, Rt: 2.20 min; (M+H) 424.2; $^1$H NMR (400 MHz, DMSO-d$_6$, 90° C.) δ 8.00-7.93 (m, 2H), 7.64-7.55 (m, 3H), 6.69 (s, 1H), 4.80-4.71 (m, 1H), 4.45-4.38 (m, 1H), 2.94-2.83 (m, 2H), 2.25-2.12 (m, 2H), 1.75-1.63 (m, 1H), 1.58-1.47 (m, 4H), 1.32-1.25 (m, 1H), 1.14-1.06 (m, 3H), 0.83 (d, J=7.0 Hz, 3H).

The following compounds were prepared analogously:

EXAMPLE 17

(R)-3,3,3-Trifluoro-1-(4-{1-[5-(4-fluoro-phenyl)-4H-[1,2,4]triazol-3-yl]-cyclopropyl}-3-methyl-piperidin-1-yl)-2-hydroxy-2-methyl-propan-1-one ("A17"), Mixture of Diastereomers

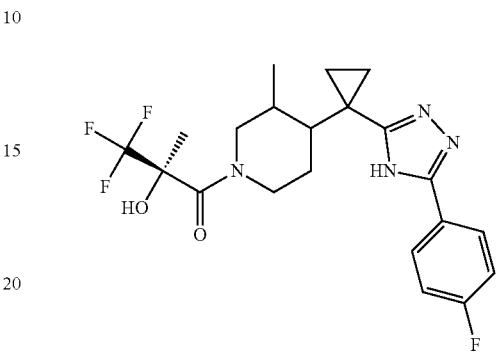

Yield: 110 mg (41%) colourless solid; LC/MS, Rt: 2.07 min; (M+H) 441.2

Preparation of (R)-3,3,3-Trifluoro-1-((3R,4R)-4-{1-[5-(4-fluoro-phenyl)-4H-[1,2,4]triazol-3-yl]-cyclopropyl}-3-methyl-piperidin-1-yl)-2-hydroxy-2-methyl-propan-1-one ("A18")

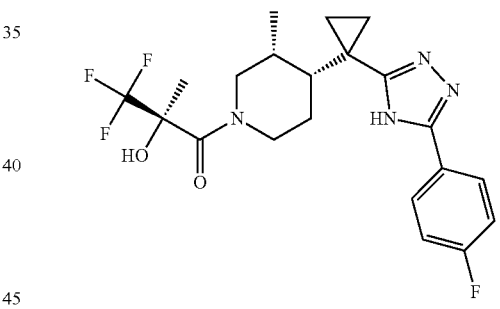

And (R)-3,3,3-Trifluoro-1-((3S,4S)-4-{1-[5-(4-fluoro-phenyl)-4H-[1,2,4]triazol-3-yl]-cyclopropyl}-3-methyl-piperidin-1-yl)-2-hydroxy-2-methyl-propan-1-one ("A19")

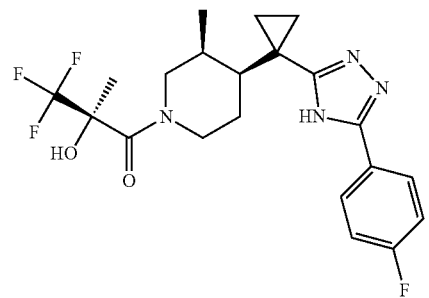 [SMILES: C[C@@H]1CN(C(=O)[C@@](C)(O)C(F)(F)F)CC[C@@H]1C1(c2nnc(-c3ccc(F)cc3)[nH]2)CC1]

The preparative separation of the diastereomers of example 17 was performed by SFC (column: ChiralPak AD-H; eluent: CO₂:methanol—90:10). The combined fractions were evaporated to dryness. The oily residue was dissolved in acetonitrile, diluted with water and lyophilized.

"A18": 25.5 mg colorless solid; LC/MS, Rt: 2.08 min; (M+H) 441.2; ¹H NMR (400 MHz, DMSO-d₆, 90° C.) δ 13.51 (s, 1H), 8.13-7.93 (m, 2H), 7.38-7.16 (m, 2H), 6.68 (s, 1H), 4.74 (d, J=13.8 Hz, 1H), 4.34 (d, J=13.0 Hz, 1H), 2.97-2.79 (m, 2H), 2.40 (dt, J=12.2, 3.9 Hz, 1H), 2.17-2.00 (m, 1H), 1.71-1.50 (m, 4H), 1.50-1.39 (m, 1H), 1.39-1.20 (m, 1H), 1.06-0.77 (m, 5H), 0.77-0.62 (m, 1H).

"A19": 26 mg colorless solid; LC/MS, Rt: 2.07 min; (M+H) 441.2; ¹H NMR (400 MHz, DMSO-d₆, 90° C.) δ 13.56 (s, 1H), 8.13-7.91 (m, 2H), 7.40-7.16 (m, 2H), 6.67 (s, 1H), 4.74 (d, J=13.2 Hz, 1H), 4.39 (d, J=13.1 Hz, 1H), 2.98-2.74 (m, 2H), 2.38 (dt, J=12.4, 4.0 Hz, 1H), 2.18-1.96 (m, 1H), 1.67-1.48 (m, 4H), 1.47-1.36 (m, 1H), 1.33-1.19 (m, 1H), 1.05-0.88 (m, 2H), 0.84 (d, J=7.0 Hz, 3H), 0.78-0.55 (m, 1H).

EXAMPLE 20

(R)-3,3,3-Trifluoro-2-hydroxy-2-methyl-1-{3-methyl-4-[1-(5-p-tolyl-4H-[1,2,4]triazol-3-yl)-cyclopropyl]-piperidin-1-yl}-propan-1-one ("A20"), Mixture of Diastereomers

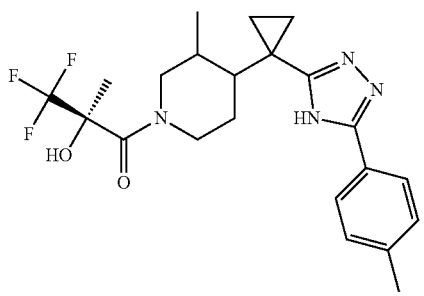 [SMILES: Cc1ccc(-c2nnc(C3(C4CCN(C(=O)[C@@](C)(O)C(F)(F)F)CC4C)CC3)[nH]2)cc1]

Yield: 52 mg (20%) beige oil; LC/MS, Rt: 2.10 min; (M+H) 437.3.

Preparation of (R)-3,3,3-Trifluoro-2-hydroxy-2-methyl-1-{(3R,4R)-3-methyl-4-[1-(5-p-tolyl-4H-[1,2,4]triazol-3-yl)-cyclopropyl]-piperidin-1-yl}-propan-1-one ("A21")

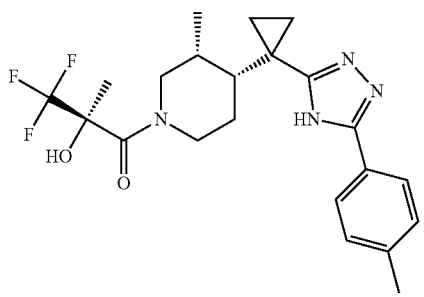 [SMILES: Cc1ccc(-c2nnc(C3([C@@H]4CCN(C(=O)[C@@](C)(O)C(F)(F)F)C[C@@H]4C)CC3)[nH]2)cc1]

And (R)-3,3,3-Trifluoro-2-hydroxy-2-methyl-1-{(3S,4S)-3-methyl-4-[1-(5-p-tolyl-4H-[1,2,4]triazol-3-yl)-cyclopropyl]-piperidin-1-yl}-propan-1-one ("A22")

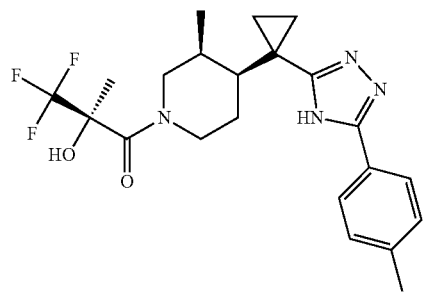 [SMILES: Cc1ccc(-c2nnc(C3([C@H]4CCN(C(=O)[C@@](C)(O)C(F)(F)F)C[C@H]4C)CC3)[nH]2)cc1]

The preparative separation of the diastereomers of example 20 was performed by SFC (column: ChiralPak AD-H; eluent: CO₂:methanol (containing 0.5% diethylamine)—80:20). The combined fractions were evaporated to dryness. The oily residue was dissolved in acetonitrile, diluted with water and lyophilized.

"A21": 18 mg colorless solid; LC/MS, Rt: 2.09 min; (M+H) 437.2; ¹H NMR (400 MHz, DMSO-d₆, 90° C.) δ 13.33 (s, br, 1H), 7.83 (d, J=8.1 Hz, 2H), 7.24 (d, J=7.9 Hz, 2H), 6.62 (s, 1H), 4.69 (d, J=13.0 Hz, 1H), 4.30 (d, J=12.8 Hz, 1H), 2.94-2.75 (m, 2H), 2.42-2.28 (m, 4H), 2.13-1.98 (m, 1H), 1.62-1.46 (m, 4H), 1.44-1.34 (m, 1H), 1.29-1.16 (m, 1H), 0.95-0.84 (m, 2H), 0.80 (d, J=7.0 Hz, 3H), 0.73-0.59 (m, 1H).

"A22": 18 mg colorless solid; LC/MS, Rt: 2.08 min; (M+H) 437.2; ¹H NMR (400 MHz, DMSO-d₆, 90° C.) δ 13.44 (s, br, 1H), 7.83 (d, J=8.1 Hz, 2H), 7.24 (d, J=7.9 Hz, 2H), 6.62 (s, 1H), 4.69 (d, J=12.5 Hz, 1H), 4.34 (d, J=12.8 Hz, 1H), 2.91-2.76 (m, 2H), 2.41-2.27 (m, 4H), 2.12-1.97 (m, 1H), 1.59-1.44 (m, 4H), 1.43-1.33 (m, 1H), 1.29-1.15 (m, 1H), 0.98-0.84 (m, 2H), 0.80 (d, J=7.0 Hz, 3H), 0.71-0.60 (m, 1H).

EXAMPLE 23

(R)-3,3,3-Trifluoro-2-hydroxy-2-methyl-1-{3-methyl-4-[1-(5-p-tolyl-[1,3,4]oxa-diazol-2-yl)-cyclopropyl]-piperidin-1-yl}-propan-1-one ("A23"), Mixture of Diastereomers

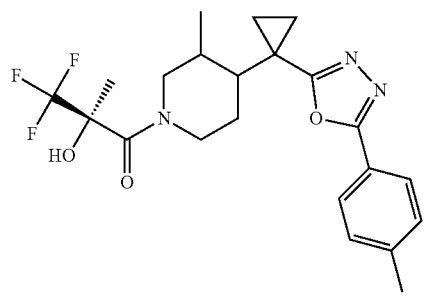 [SMILES: Cc1ccc(-c2nnc(C3(C4CCN(C(=O)[C@@](C)(O)C(F)(F)F)CC4C)CC3)o2)cc1]

Yield: 144 mg (52%) beige oil; LC/MS, Rt: 2.35 min; (M+H) 438.2.

Preparation of (R)-3,3,3-Trifluoro-2-hydroxy-2-methyl-1-{(3R,4R)-3-methyl-4-[1-(5-p-tolyl-[1,3,4]oxadiazol-2-yl)-cyclopropyl]-piperidin-1-yl}-propan-1-one ("A24")

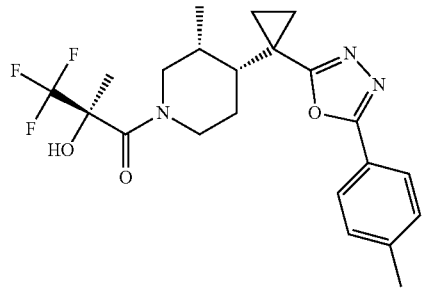 [SMILES: Cc1ccc(-c2nnc(C3([C@@H]4CCN(C(=O)[C@@](C)(O)C(F)(F)F)C[C@@H]4C)CC3)o2)cc1]

And (R)-3,3,3-Trifluoro-2-hydroxy-2-methyl-1-{(3S,4S)-3-methyl-4-[1-(5-p-tolyl-[1,3,4]oxadiazol-2-yl)-cyclopropyl]-piperidin-1-yl}-propan-1-one ("A25")

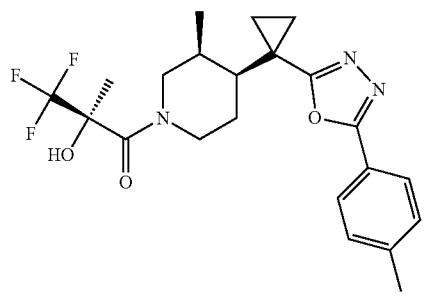 [SMILES: Cc1ccc(-c2nnc(C3([C@H]4CCN(C(=O)[C@@](C)(O)C(F)(F)F)C[C@H]4C)CC3)o2)cc1]

The preparative separation of the diastereomers of example 23 was performed by SFC (column: ChiralPak AD-H; eluent: $CO_2$:ethanol—80:20). The combined fractions were evaporated to dryness. The oily residue was dissolved in acetonitrile, diluted with water and lyophilized.

"A24": 45 mg colorless solid; LC/MS, Rt: 2.34 min; (M+H) 438.1; $^1$H NMR (400 MHz, DMSO-$d_6$, 90° C.) δ 7.83 (d, J=8.2 Hz, 2H), 7.37 (d, J=8.0 Hz, 2H), 6.66 (s, 1H), 4.72 (d, J=12.6 Hz, 1H), 4.34 (d, J=12.9 Hz, 1H), 2.94-2.76 (m, 2H), 2.39 (s, 3H), 2.22 (dt, J=12.4, 3.8 Hz, 1H), 2.18-2.10 (m, 1H), 1.66 (qd, J=12.6, 4.3 Hz, 1H), 1.58-1.44 (m, 4H), 1.33-1.21 (m, 1H), 1.14-1.01 (m, 3H), 0.81 (d, J=7.0 Hz, 3H).

"A25": 45 mg colorless solid; LC/MS, Rt: 2.33 min; (M+H) 438.2; $^1$H NMR (400 MHz, DMSO-$d_6$, 90° C.) δ 7.83 (d, J=8.2 Hz, 2H), 7.37 (d, J=8.0 Hz, 2H), 6.67 (s, 1H), 4.73 (d, J=12.8 Hz, 1H), 4.39 (d, J=13.0 Hz, 1H), 2.92-2.79 (m, 2H), 2.39 (s, 3H), 2.23-2.10 (m, 2H), 1.66 (qd, J=12.6, 4.4 Hz, 1H), 1.57-1.44 (m, 4H), 1.31-1.20 (m, 1H), 1.14-1.02 (m, 3H), 0.81 (d, J=6.9 Hz, 3H).

EXAMPLE 26

(R)-3,3,3-Trifluoro-2-hydroxy-1-(4-{1-[5-(4-methoxy-phenyl)-4H-[1,2,4]triazol-3-yl]-cyclopropyl}-3-methyl-piperidin-1-yl)-2-methyl-propan-1-one ("A26"), Mixture of Diastereomers

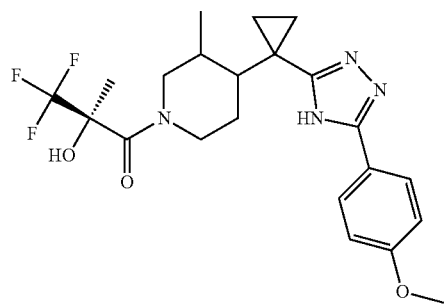 [SMILES: COc1ccc(-c2nnc(C3(C4CCN(C(=O)[C@@](C)(O)C(F)(F)F)CC4C)CC3)[nH]2)cc1]

Yield: 60 mg (21%) beige oil; LC/MS, Rt: 1.96 min; (M+H) 453.2

Preparation of (R)-3,3,3-Trifluoro-2-hydroxy-1-((3R,4R)-4-{1-[5-(4-methoxy-phenyl)-4H-[1,2,4]triazol-3-yl]-cyclopropyl}-3-methyl-piperidin-1-yl)-2-methyl-propan-1-one ("A27")

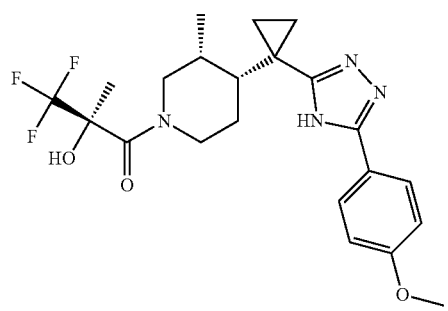 [SMILES: COc1ccc(-c2nnc(C3([C@@H]4CCN(C(=O)[C@@](C)(O)C(F)(F)F)C[C@@H]4C)CC3)[nH]2)cc1]

And (R)-3,3,3-Trifluoro-2-hydroxy-1-((3S,4S)-4-{1-[5-(4-methoxy-phenyl)-4H-[1,2,4]triazol-3-yl]-cyclopropyl}-3-methyl-piperidin-1-yl)-2-methyl-propan-1-one ("A28")

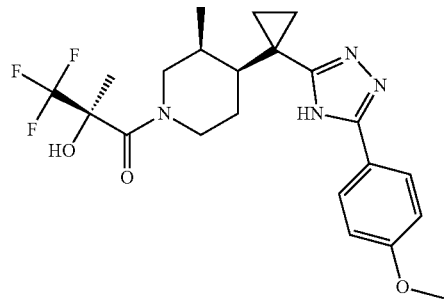 [SMILES: COc1ccc(-c2nnc(C3([C@H]4CCN(C(=O)[C@@](C)(O)C(F)(F)F)C[C@H]4C)CC3)[nH]2)cc1]

The preparative separation of the diastereomers of example 26 was performed by SFC (column: Luc Cellulose- 2; eluent: CO₂:ethanol (containing 0.5% diethylamine)—85:15). The combined fractions were evaporated to dryness. The oily residue was dissolved in acetonitrile, diluted with water and lyophilized.

"A27": 21 mg colorless solid; LC/MS, Rt: 1.97 min; (M+H) 453.2; ¹H NMR (400 MHz, DMSO-d₆, 90° C.) δ 13.38 (s, br, 1H), 7.90 (d, J=8.9 Hz, 2H), 7.02 (d, J=8.8 Hz, 2H), 6.66 (s, 1H), 4.72 (d, J=12.5 Hz, 1H), 4.32 (dt, J=12.8, 2.1 Hz, 1H), 3.83 (s, 3H), 2.97-2.77 (m, 2H), 2.38 (dt, J=12.3, 3.8 Hz, 1H), 2.16-2.04 (m, 1H), 1.64-1.48 (m, 4H), 1.42 (dq, J=12.8, 2.9 Hz, 1H), 1.26-1.15 (m, 1H), 0.96-0.86 (m, 2H), 0.82 (d, J=7.0 Hz, 3H), 0.74-0.61 (m, 1H).

"A28": 21 mg colorless solid; LC/MS, Rt: 1.96 min; (M+H) 453.2; ¹H NMR (400 MHz, DMSO-d₆, 90° C.) δ 13.39 (s, br, 1H), 7.90 (d, J=8.9 Hz, 2H), 7.02 (d, J=8.8 Hz, 2H), 6.65 (s, 1H), 4.72 (d, J=11.8 Hz, 1H), 4.37 (d, J=12.9 Hz, 1H), 3.83 (s, 3H), 2.95-2.79 (m, 2H), 2.37 (dt, J=12.4, 3.8 Hz, 1H), 2.15-2.02 (m, 1H), 1.62-1.47 (m, 4H), 1.45-1.37 (m, 1H), 1.32-1.18 (m, 1H), 0.96-0.86 (m, 2H), 0.83 (d, J=7.0 Hz, 3H), 0.74-0.64 (m, 1H).

EXAMPLE 29

(R)-3,3,3-Trifluoro-2-hydroxy-1-(4-{1-[5-(4-methoxy-phenyl)-[1,3,4]oxadiazol-2-yl]-cyclopropyl}-3-methyl-piperidin-1-yl)-2-methyl-propan-1-one ("A29"), Mixture of Diastereomers

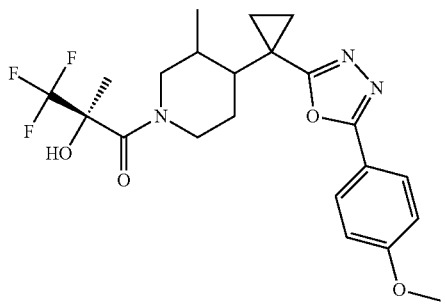 [SMILES: COc1ccc(-c2nnc(C3(C4CCN(C(=O)[C@@](C)(O)C(F)(F)F)CC4C)CC3)o2)cc1]

Yield: 108 mg (39%) beige oil; LC/MS, Rt: 2.22 min; (M+H) 454.2

Preparation of (R)-3,3,3-Trifluoro-2-hydroxy-1-((3R,4R)-4-{1-[5-(4-methoxy-phenyl)-[1,3,4]oxadiazol-2-yl]-cyclopropyl}-3-methyl-piperidin-1-yl)-2-methyl-propan-1-one ("A30")

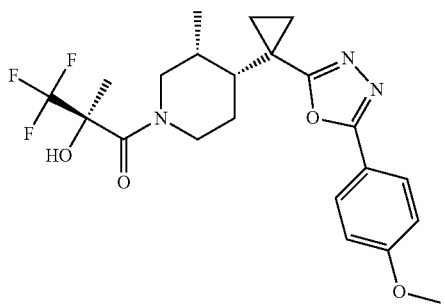 [SMILES: COc1ccc(-c2nnc(C3([C@@H]4CCN(C(=O)[C@@](C)(O)C(F)(F)F)C[C@@H]4C)CC3)o2)cc1]

And (R)-3,3,3-Trifluoro-2-hydroxy-1-((3S,4S)-4-{1-[5-(4-methoxy-phenyl)-[1,3,4]oxadiazol-2-yl]-cyclopropyl}-3-methyl-piperidin-1-yl)-2-methyl-propan-1-one ("A31")

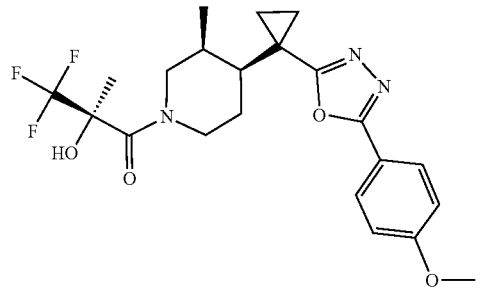 [SMILES: COc1ccc(-c2nnc(C3([C@H]4CCN(C(=O)[C@@](C)(O)C(F)(F)F)C[C@H]4C)CC3)o2)cc1]

The preparative separation of the diastereomers of example 29 was performed by SFC (column: ChiralPak AD-H; eluent: CO₂:ethanol—75:25). The combined fractions were evaporated to dryness. The oily residue was dissolved in acetonitrile, diluted with water and lyophilized.

"A30": 34 mg colorless solid; LC/MS, Rt: 2.23 min; (M+H) 454.2; ¹H NMR (400 MHz, DMSO-d₆, 90° C.) δ 7.90 (d, J=8.9 Hz, 2H), 7.13 (d, J=8.9 Hz, 2H), 6.69 (s, 1H), 4.75 (d, J=12.4 Hz, 1H), 4.37 (dt, J=13.0, 2.2 Hz, 1H), 3.87 (s, 3H), 2.96-2.82 (m, 2H), 2.24 (dt, J=12.4, 3.8 Hz, 1H), 2.20-2.11 (m, 1H), 1.68 (qd, J=12.6, 4.2 Hz, 1H), 1.57 (s, 3H), 1.51 (dq, J=12.8, 3.3 Hz, 1H), 1.32-1.24 (m, 1H), 1.16-1.03 (m, 3H), 0.83 (d, J=7.0 Hz, 3H).

"A31": 35.5 mg colorless solid; LC/MS, Rt: 2.22 min; (M+H) 454.2; ¹H NMR (400 MHz, DMSO-d₆, 90° C.) δ 7.90 (d, J=8.9 Hz, 2H), 7.13 (d, J=8.9 Hz, 2H), 6.70 (s, 1H), 4.75 (d, J=12.6 Hz, 1H), 4.42 (d, J=13.0 Hz, 1H), 3.87 (s, 3H), 2.96-2.81 (m, 2H), 2.26-2.11 (m, 2H), 1.68 (qd, J=12.5, 4.4 Hz, 1H), 1.55 (s, 3H), 1.54-1.46 (m, 1H), 1.30-1.23 (m, 1H), 1.15-1.02 (m, 3H), 0.83 (d, J=6.9 Hz, 3H).

EXAMPLE 32

(R)-1-(4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one ("A32"), Mixture of Diastereomers

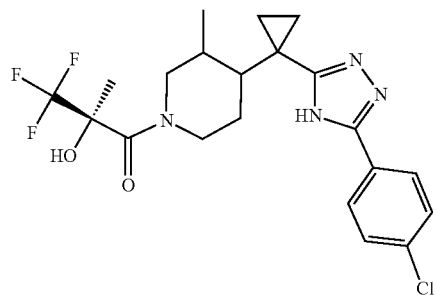 [SMILES: CC1CN(C(=O)[C@@](C)(O)C(F)(F)F)CCC1C1(c2nnc(-c3ccc(Cl)cc3)[nH]2)CC1]

Yield: 68 mg (25%) beige oil; LC/MS, Rt: 2.21 min; (M+H) 457.2/459.1

Preparation of (R)-1-((3R,4R)-4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one ("A33")

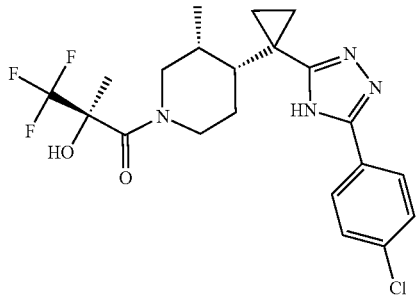 [SMILES: C[C@H]1CN(C(=O)[C@@](C)(O)C(F)(F)F)CC[C@H]1C1(c2nnc(-c3ccc(Cl)cc3)[nH]2)CC1]

And (R)-1-((3S,4S)-4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one ("A34")

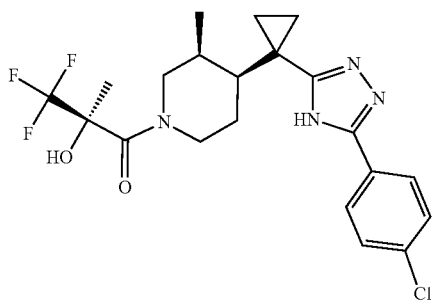 [SMILES: C[C@@H]1CN(C(=O)[C@@](C)(O)C(F)(F)F)CC[C@@H]1C1(c2nnc(-c3ccc(Cl)cc3)[nH]2)CC1]

The preparative separation of the diastereomers of example 32 was performed by SFC (column: ChiralPak AD-H; eluent: CO$_2$:methanol (containing 0.5% diethylamine)—85:15). The combined fractions were evaporated to dryness. The oily residue was dissolved in acetonitrile, diluted with water and lyophilized.

"A33": 20 mg colorless solid; LC/MS, Rt: 2.21 min; (M+H) 457.2/459.1; $^1$H NMR (400 MHz, DMSO-d$_6$, 90° C.) δ 12.82 (s, br, 1H), 7.98 (d, J=8.6 Hz, 2H), 7.50 (d, J=8.6 Hz, 2H), 6.66 (s, 1H), 4.72 (d, J=13.4 Hz, 1H), 4.32 (d, J=12.8 Hz, 1H), 2.90 (t, J=13.0 Hz, 1H), 2.84 (d, J=12.2 Hz, 1H), 2.38 (dt, J=12.2, 3.9 Hz, 1H), 2.09-2.00 (m, 1H), 1.62-1.48 (m, 4H), 1.48-1.39 (m, 1H), 1.30-1.21 (m, 1H), 0.99-0.90 (m, 2H), 0.82 (d, J=7.0 Hz, 3H), 0.76-0.65 (m, 1H).

"A34": 21 mg colorless solid; LC/MS, Rt: 2.21 min; (M+H) 457.2/459.1; $^1$H NMR (400 MHz, DMSO-d$_6$, 90° C.) δ 13.28 (s, br, 1H), 7.98 (d, J=8.6 Hz, 2H), 7.50 (d, J=8.6 Hz, 2H), 6.66 (s, 1H), 4.72 (d, J=12.2 Hz, 1H), 4.37 (d, J=13.0 Hz, 1H), 2.95-2.76 (m, 2H), 2.37 (dt, J=12.3, 3.8 Hz, 1H), 2.11-1.97 (m, 1H), 1.65-1.46 (m, 4H), 1.46-1.36 (m, 1H), 1.32-1.20 (m, 1H), 0.99-0.88 (m, 2H), 0.82 (d, J=7.0 Hz, 3H), 0.75-0.65 (m, 1H).

EXAMPLE 35

(R)-1-(4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one ("A35"), Mixture of Diastereomers

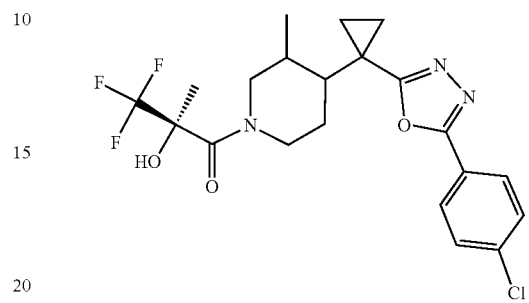

Yield: 170 mg (58%) beige oil; LC/MS, Rt: 2.39 min; (M+H) 458.1/460.1.

Preparation of (R)-1-((3R,4R)-4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one ("A36")

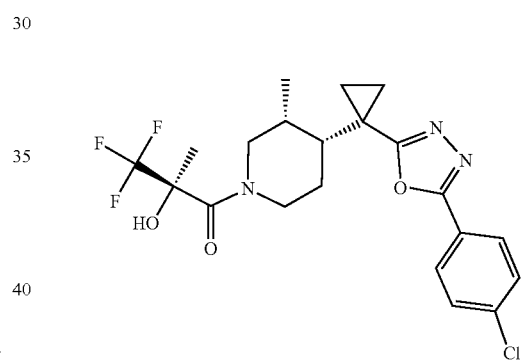

And (R)-1-((3S,4S)-4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one ("A37")

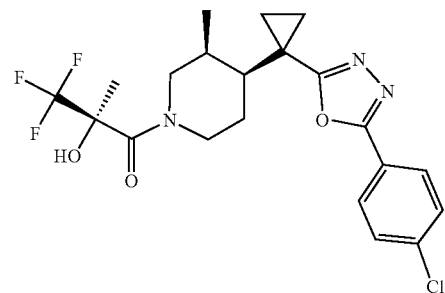 [SMILES: C[C@@H]1CN(C(=O)[C@@](C)(O)C(F)(F)F)CC[C@@H]1C1(c2nnc(-c3ccc(Cl)cc3)o2)CC1]

The preparative separation of the diastereomers of example 35 was performed by SFC (column: ChiralPak AD-H; eluent: CO$_2$:ethanol—75:25). The combined fractions were evaporated to dryness. The oily residue was dissolved in acetonitrile, diluted with water and lyophilized.

"A36": 53 mg colorless solid; LC/MS, Rt: 2.40 min; (M+H) 458.1/460.1; $^1$H NMR (400 MHz, DMSO-d$_6$, 90° C.) δ 8.03-7.94 (m, 2H), 7.68-7.60 (m, 2H), 6.69 (s, 1H), 4.75 (d, J=12.4 Hz, 1H), 4.37 (d, J=12.9 Hz, 1H), 2.96-2.81 (m, 2H), 2.27 (dt, J=12.5, 3.9 Hz, 1H), 2.23-2.13 (m, 1H), 1.68 (qd, J=12.6, 4.3 Hz, 1H), 1.61-1.55 (m, 3H), 1.55-1.45 (m, 1H), 1.40-1.25 (m, 1H), 1.18-1.02 (m, 3H), 0.83 (d, J=7.0 Hz, 3H).

"A37": 54.5 mg colorless solid; LC/MS, Rt: 2.39 min; (M+H) 458.1/460.1; $^1$H NMR (400 MHz, DMSO-d$_6$, 90° C.) δ 8.04-7.93 (m, 2H), 7.70-7.57 (m, 2H), 6.70 (s, 1H), 4.75 (d, J=12.4 Hz, 1H), 4.42 (d, J=13.1 Hz, 1H), 2.96-2.83 (m, 2H), 2.24 (dt, J=12.5, 3.8 Hz, 1H), 2.21-2.12 (m, 1H), 1.67 (qd, J=12.6, 4.2 Hz, 1H), 1.55 (s, 3H), 1.53-1.45 (m, 1H), 1.34-1.25 (m, 1H), 1.16-1.06 (m, 3H), 0.84 (d, J=7.0 Hz, 3H).

EXAMPLE 38

(R)-3,3,3-Trifluoro-2-hydroxy-1-(4-{1-[5-(6-methoxy-pyridin-3-yl)-4H-[1,2,4]triazol-3-yl]-cyclopropyl}-3-methyl-piperidin-1-yl)-2-methyl-propan-1-one ("A38"), Mixture of Diastereomers

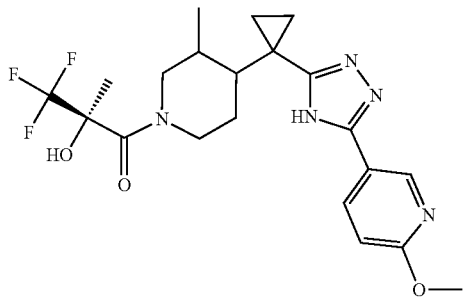 [SMILES: COc1ccc(-c2nnc(C3(C4CCN(C(=O)[C@@](C)(O)C(F)(F)F)CC4C)CC3)[nH]2)cn1]

Yield: 103 mg (29%) beige oil; LC/MS, Rt: 1.91 min; (M+H) 454.2 Preparation of (R)-3,3,3-Trifluoro-2-hydroxy-1-((3R,4R)-4-{1-[5-(6-methoxy-pyridin-3-yl)-4H-[1,2,4]triazol-3-yl]-cyclopropyl}-3-methyl-piperidin-1-yl)-2-methyl-propan-1-one ("A39")

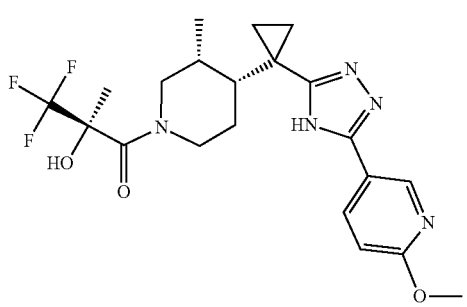 [SMILES: COc1ccc(-c2nnc(C3([C@@H]4CCN(C(=O)[C@@](C)(O)C(F)(F)F)C[C@@H]4C)CC3)[nH]2)cn1]

And (R)-3,3,3-Trifluoro-2-hydroxy-1-((3S,4S)-4-{1-[5-(6-methoxy-pyridin-3-yl)-4H-[1,2,4]triazol-3-yl]-cyclopropyl}-3-methyl-piperidin-1-yl)-2-methyl-propan-1-one ("A40")

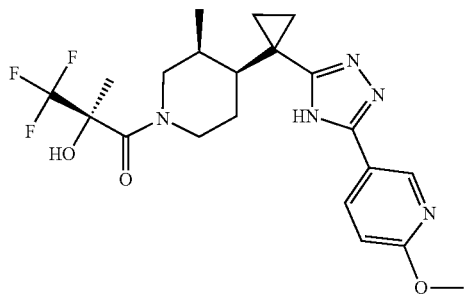 [SMILES: COc1ccc(-c2nnc(C3([C@H]4CCN(C(=O)[C@@](C)(O)C(F)(F)F)C[C@H]4C)CC3)[nH]2)cn1]

The preparative separation of the diastereomers of example 38 was performed by SFC (column: ChiralPak AD-H; eluent: CO$_2$:methanol (containing 0.5% diethylamine)—65:35). The combined fractions were evaporated to dryness. The oily residue was dissolved in acetonitrile, diluted with water and lyophilized.

"A39": 40 mg colorless solid; LC/MS, Rt: 1.90 min; (M+H) 454.2; $^1$H NMR (500 MHz, DMSO-d$_6$) δ 13.54 (s, br, 1H), 8.77-8.70 (m, 1H), 8.19 (dd, J=8.6, 2.0 Hz, 1H), 7.03 (s, 1H), 6.92 (d, J=8.6 Hz, 1H), 4.94-4.18 (m, 2H), 3.91 (s, 3H), 2.97 (s, 1H), 2.77-2.62 (m, 1H), 2.48-2.37 (m, 1H), 1.97 (s, 1H), 1.54 (s, 3H), 1.49-1.37 (m, 2H), 1.30-1.23 (m, 1H), 1.00-0.91 (m, 2H), 0.77 (s, 3H), 0.60 (d, J=10.5 Hz, 1H).

"A40": 30 mg colorless solid; LC/MS, Rt: 1.90 min; (M+H) 454.2; $^1$H NMR (500 MHz, DMSO-d$_6$) δ 13.66 (s, br, 1H), 8.78-8.68 (m, 1H), 8.19 (dd, J=8.6, 2.4 Hz, 1H), 6.98 (s, 1H), 6.92 (d, J=8.7 Hz, 1H), 4.97-4.15 (m, 2H), 3.91 (s, 3H), 3.17-2.84 (m, 1H), 2.75-2.63 (m, 1H), 2.44 (d, J=11.3 Hz, 1H), 2.03-1.90 (m, 1H), 1.51 (s, 3H), 1.50-1.32 (m, 2H), 1.32-1.22 (m, 1H), 0.98-0.71 (m, 5H), 0.64-0.56 (m, 1H).

EXAMPLE 41

(R)-3,3,3-Trifluoro-2-hydroxy-1-(4-{1-[5-(6-methoxy-pyridin-3-yl)-[1,3,4]oxadiazol-2-yl]-cyclopropyl}-3-methyl-piperidin-1-yl)-2-methyl-propan-1-one ("A41"), Mixture of Diastereomers

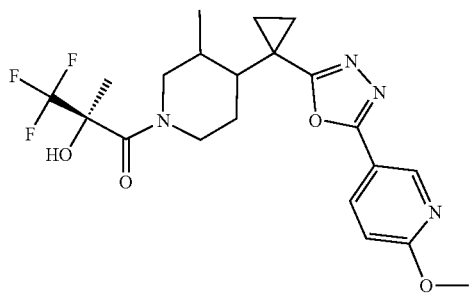 [SMILES: COc1ccc(-c2nnc(C3(C4CCN(C(=O)[C@@](C)(O)C(F)(F)F)CC4C)CC3)o2)cn1]

Yield: 101 mg (29%) beige oil; LC/MS, Rt: 2.16 min; (M+H) 455.2 Preparation of (R)-3,3,3-Trifluoro-2-hydroxy- 1-((3R,4R)-4-{1-[5-(6-methoxy-pyridin-3-yl)-[1,3,4]oxadiazol-2-yl]-cyclopropyl}-3-methyl-piperidin-1-yl)-2-methyl-propan-1-one ("A42")

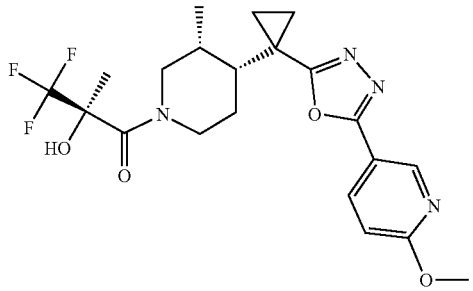 [SMILES: COc1ccc(-c2nnc(C3([C@@H]4CCN(C(=O)[C@@](C)(O)C(F)(F)F)C[C@@H]4C)CC3)o2)cn1]

And (R)-3,3,3-Trifluoro-2-hydroxy-1-((3S,4S)-4-{1-[5-(6-methoxy-pyridin-3-yl)-[1,3,4]oxadiazol-2-yl]-cyclopropyl}-3-methyl-piperidin-1-yl)-2-methyl-propan-1-one ("A43")

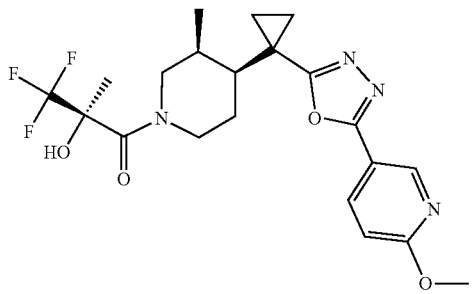 [SMILES: COc1ccc(-c2nnc(C3([C@H]4CCN(C(=O)[C@@](C)(O)C(F)(F)F)C[C@H]4C)CC3)o2)cn1]

The preparative separation of the diastereomers of example 41 was performed by SFC (column: ChiralPak AD-H; eluent: $CO_2$:ethanol—80:20). The combined fractions were evaporated to dryness. The oily residue was dissolved in acetonitrile, diluted with water and lyophilized.

"A42": 32.5 mg colorless solid; LC/MS, Rt: 2.16 min; (M+H) 455.2; $^1$H NMR (500 MHz, DMSO-$d_6$) δ 8.81-8.77 (m, 1H), 8.23 (dd, J=8.7, 2.4 Hz, 1H), 7.14-6.98 (m, 2H), 5.01-4.19 (m, 2H), 3.96 (s, 3H), 3.10-2.66 (m, 2H), 2.33 (s, 1H), 2.20-2.11 (m, 1H), 1.59 (s, 1H), 1.54 (s, 3H), 1.46 (d, J=11.4 Hz, 1H), 1.37-1.28 (m, 1H), 1.17-1.06 (m, 2H), 1.06-0.98 (m, 1H), 0.84-0.70 (m, 3H).

"A43": 32 mg colorless solid; LC/MS, Rt: 2.15 min; (M+H) 455.2; $^1$H NMR (500 MHz, DMSO-$d_6$) δ 8.78 (d, J=1.8 Hz, 1H), 8.23 (dd, J=8.7, 2.3 Hz, 1H), 7.07-6.93 (m, 2H), 4.96-4.17 (m, 2H), 3.96 (s, 3H), 3.19-2.55 (m, 2H), 2.29 (d, J=11.9 Hz, 1H), 2.21-2.09 (m, 1H), 1.74-1.54 (m, 1H), 1.52 (s, 3H), 1.50-1.39 (m, 1H), 1.36-1.29 (m, 1H), 1.15-0.98 (m, 3H), 0.96-0.68 (m, 3H).

Pharmacological Data

TABLE 1

Inhibition of PDHK of some representative compounds of the formula I

| Compound No. | $IC_{50}$ PDHK2 (enzyme assay) [M] | Binding (ITC) KD [M] | $IC_{50}$ (cell data) [M] |
|---|---|---|---|
| "A1" | 5.90E−07 | 1.10E−07 | 3.00E−06 |
| "A2" | 4.90E−β7 | 1.80E−07 | 2.00E−06 |
| "A3" | 3.20E−07 | 9.80E−08 | 3.30E−06 |
| "A4" | 1.40E−06 | 2.90E−07 | 3.90E−06 |
| "A5" | 4.40E−07 | 2.00E−07 | 1.50E−06 |
| "A6" | 5.00E−07 | 2.70E−07 | 2.00E−06 |
| "A7" | 3.50E−06 | 8.50E−07 | >3.00E−05 |
| "A8" | 2.40E−06 | 6.50E−07 | 8.70E−06 |
| "A9" | 7.20E−07 | 5.00E−08 | 6.50E−07 |
| "A10" | 4.00E−07 | 1.20E−07 | 2.00E−06 |
| "A11" | 3.70E−07 | 8.30E−09 | 1.20E−07 |
| "A12" | 2.70E−07 | 8.70E−09 | 5.60E−08 |
| "A13" | 6.60E−06 | | |
| "A14" | 1.30E−07 | <2.00E−09 | 1.90E−08 |
| "A15" | 1.10E−05 | | 7.30E−06 |
| "A16" | 1.50E−07 | 4.90E−09 | 3.50E−08 |
| "A17" | | | |
| "A18" | 2.60E−06 | | |
| "A19" | 7.50E−08 | 4.20E−09 | 2.80E−08 |
| "A20" | | | |
| "A21" | 4.90E−06 | | |
| "A22" | 9.00E−08 | 2.60E−09 | 1.60E−08 |
| "A23" | | | |
| "A24" | 7.30E−06 | | |
| "A25" | 1.00E−07 | 4.10E−09 | 3.00E−08 |
| "A26" | | | |
| "A27" | 1.30E−05 | | |
| "A28" | 8.80E−08 | 2.50E−09 | 1.20E−08 |
| "A29" | | | |
| "A30" | 1.90E−06 | | |
| "A31" | 1.80E−07 | 3.60E−09 | 1.70E−08 |
| "A32" | | | |
| "A33" | 1.80E−05 | | |
| "A34" | 1.80E−07 | 2.80E−09 | 1.90E−08 |
| "A35" | | | |
| "A36" | 8.20E−06 | | |
| "A37" | 1.30E−07 | 2.40E−09 | 2.50E−08 |
| "A38" | | | |
| "A39" | 6.00E−06 | | |
| "A40" | 9.10E−08 | 6.50E−09 | 2.50E−08 |
| "A41" | | | |
| "A42" | 2−90E−05 | | |
| "A43" | 1.00E−07 | 3.80E−09 | 1.60E−08 |

$IC_{50}$ [M] e.g.: 5.90E−07 = 5.90 × $10^{-7}$

The compounds shown in Table 1 are particularly preferred compounds according to the invention.

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of the formula I

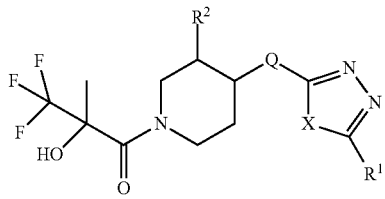

I in which
X denotes NH or O,
Q denotes $C(CH_3)_2$ or 1,1-cyclopropylene,
$R^1$ denotes H, A, Cyc, Ar or Het,
$R^2$ denotes H or $CH_3$,
$R^3$ denotes H or A',
Ar denotes phenyl, which is unsubstituted or mono-, di- or trisubstituted by Hal, $NO_2$, CN, A, $OR^3$, $S(O)_mR^3$, $N(R^3)_2$, COA, $COOR^3$, $CON(R^3)_2$, $SO_2N(R^3)_2$, $NR^3COR^3$, $NR^3SO_2A$ and/or $NR^3CON(R^3)_2$,
Het denotes a mono- or bicyclic saturated, unsaturated or aromatic heterocycle having 1 to 4 N, O and/or S atoms, which is unsubstituted or mono- or disubstituted by Hal, $NO_2$, CN, A, $OR^3$, $S(O)_mR^3$, $N(R^3)_2$, COA, $COOR^3$, $CON(R^3)_2$, $SO_2N(R^3)_2$, $NR^3COR^3$, $NR^3SO_2A$ and/or $NR^3CON(R^3)_2$,
A denotes unbranched or branched alkyl with 1-10 C-atoms, wherein one or two non-adjacent CH- and/or $CH_2$-groups may be replaced by N-, O- and/or S-atoms and/or wherein 1-7 H-atoms may be replaced by $R^4$,
$R^4$ denotes F, Cl or OH,
A' denotes unbranched or branched alkyl with 1-6 C-atoms, wherein 1-5 H-atoms may be replaced by F,
Cyc denotes cyclic alkyl with 3, 4, 5, 6 or 7 C-atoms, which is unsubstituted or monosubstituted by OH,
Hal denotes F, Cl, Br or I,
m denotes 0, 1 or 2,
and pharmaceutically acceptable salts, tautomers and stereoisomers thereof, including mixtures thereof in all ratios.

2. A compound according to claim 1 in which
$R^1$ denotes A, Cyc, Ar or Het,
and pharmaceutically acceptable salts, tautomers and stereoisomers thereof, including mixtures thereof in all ratios.

3. A compound according to claim 1, in which
$R^3$ denotes H or $CH_3$,
and pharmaceutically acceptable salts, tautomers and stereoisomers thereof, including mixtures thereof in all ratios.

4. A compound according to claim 1, in which
Ar denotes phenyl, which is unsubstituted or mono-, di- or trisubstituted by Hal, A and/or $OR^3$,
and pharmaceutically acceptable salts, tautomers and stereoisomers thereof, including mixtures thereof in all ratios.

5. A compound according to claim 1, in which
Het denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, triazolyl, oxadiazolyl or thiadiazolyl, each of which is unsubstituted or mono- or disubstituted by Hal, A, CN and/or $OR^3$,
and pharmaceutically acceptable salts, tautomers and stereoisomers thereof, including mixtures thereof in all ratios.

6. A compound according to claim 1, in which
Het denotes pyrimidyl, pyridyl, pyridazinyl or pyrazinyl, each of which is unsubstituted or mono- or disubstituted by A and/or $OR^3$,
and pharmaceutically acceptable salts, tautomers and stereoisomers thereof, including mixtures thereof in all ratios.

7. A compound according to claim 1, in which
A denotes unbranched or branched alkyl with 1-6 C-atoms, wherein 1-5 H-atoms may be replaced by F,
and pharmaceutically acceptable salts, tautomers and stereoisomers thereof, including mixtures thereof in all ratios.

8. A compound according to claim 1, in which
Cyc denotes cyclic alkyl with 3, 4, 5, 6 or 7 C-atoms,
and pharmaceutically acceptable salts, tautomers and stereoisomers thereof, including mixtures thereof in all ratios.

9. A compound according to claim 1 in which
X denotes NH or O,
Q denotes $C(CH_3)_2$ or 1,1-cyclopropylene,
$R^1$ denotes A, Cyc, Ar or Het,
$R^2$ denotes H or $CH_3$,
$R^3$ denotes H or $CH_3$, Ar denotes phenyl, which is unsubstituted or mono-, di- or trisubstituted by Hal, A and/or OR$^3$, Het denotes pyrimidyl, pyridyl, pyridazinyl or pyrazinyl, each of which is unsubstituted or mono- or disubstituted by A and/or OR$^3$, A denotes unbranched or branched alkyl with 1-6 C-atoms, wherein 1-5 H-atoms may be replaced by F, Cyc denotes cyclic alkyl with 3, 4, 5, 6 or 7 C-atoms, Hal denotes F, Cl, Br or I, and pharmaceutically acceptable salts, tautomers and stereoisomers thereof, including mixtures thereof in all ratios.

10. A compound according to claim 1, that is:

| No. | Name |
|---|---|
| "A1" | (R)-3,3,3-Trifluoro-2-hydroxy-2-methyl-1-{4-[1-(5-phenyl-1H-[1,2,4]triazol-3-yl)-cyclopropyl]-piperidin-1-yl}-propan-1-one |
| "A2" | (R)-3,3,3-Trifluoro-1-{4-{1-[5-(4-fluorophenyl)-4H-[1,2,4]triazol-3-yl]-cyclopropyl}-piperidin-1-yl}-2-hydroxy-2-methyl-propan-1-one |
| "A3" | (R)-3,3,3-Trifluoro-2-hydroxy-2-methyl-1-{4-[1-methyl-1-(5-phenyl-4H-[1,2,4]triazol-3-yl)-ethyl]-piperidin-1-yl}-propan-1-one |
| "A4" | (R)-1-{4-[1-(5-Cyclohexyl-4H-[1,2,4]triazol-3-yl)-1-methyl-ethyl]-piperidin-1-yl}-3,3,3-trifluoro-2-hydroxy-2-methyl-propan-1-one |
| "A5" | (R)-3,3,3-Trifluoro-2-hydroxy-2-methyl-1-{4-[1-(5-phenyl-[1,3,4]oxadiazol-2-yl)-cyclopropyl]-piperidin-1-yl}-propan-1-one |
| "A6" | (R)-3,3,3-Trifluoro-1-{4-{1-[5-(4-fluoro-phenyl)-[1,3,4]oxadiazol-2-yl]-cyclopropyl}-piperidin-1-yl}-2-hydroxy-2-methyl-propan-1-one |
| "A7" | (R)-3,3,3-Trifluoro-2-hydroxy-2-methyl-1-{4-[1-(5-methyl-[1,3,4]oxadizaol-2-yl)-cyclopropyl]-piperidin-1-yl}-propan-1-one |
| "A8" | (R)-1-{4-[1-(5-tert-Butyl-[1,3,4]oxadiazol-2-yl)-cyclopropyl]-piperidin-1-yl}-3,3,3-trifluoro-2-hydroxy-2-methyl-propan-1-one |
| "A9" | (R)-3,3,3-Trifluoro-2-hydroxy-2-methyl-1-{4-[1-methyl-1-(5-phenyl-[1,3,4]oxadiazol-2-yl)-ethyl]-piperidin-1-yl}-propan-1-one |
| "A10" | (R)-1-{4-[1-(5-Cyclohexyl-[1,3,4]oxadiazol-2-yl)-1-methyl-ethyl]-piperidin-1-yl}-3,3,3-trifluoro-2-hydroxy-2-methyl-propan-1-one |
| "A11" | (R)-3,3,3-Trifluoro-2-hydroxy-2-methyl-1-{3-methyl-4-[1-(5-phenyl-1H-[1,2,4]triazol-3-yl)-cyclopropyl]-piperidin-1-yl}-propan-1-one |
| "A12" | (R)-3,3,3-Trifluoro-2-hydroxy-2-methyl-1-{3-methyl-4-[1-(5-phenyl-[1,3,4]oxadizaol-2-yl)-cyclopropyl]-piperidin-1-yl}-propan-1-one |
| "A13" | (R)-3,3,3-Trifluoro-2-hydroxy-2-methyl-1-{(3R,4R)-3-methyl-4-[1-(5-phenyl-4H-[1,2,4]triazol-3-yl)-cyclopropyl]-piperidin-1-yl}-propan-1-one |
| "A14" | (R)-3,3,3-Trifluoro-2-hydroxy-2-methyl-1-{(3S,4S)-3-methyl-4-[1-(5-phenyl-4H-[1,2,4]triazol-3-yl)-cyclopropyl]-piperidin-1-yl}-propan-1-one |
| "A15" | (R)-3,3,3-Trifluoro-2-hydroxy-2-methyl-1-{(S)-3-methyl-4-[1-(5-phenyl-[1,3,4]oxadiazol-2-yl)-cyclopropyl]-piperidin-1-yl}-propan-1-one |
| "A16" | (R)-3,3,3-Trifluoro-2-hydroxy-2-methyl-1-{(R)-3-methyl-4-[1-(5-phenyl-[1,3,4]oxadiazol-2-yl)-cyclopropyl]-piperidin-1-yl}-propan-1-one |
| "A17" | (R)-3,3,3-Trifluoro-1-(4-{1-[5-(4-fluoro-phenyl)-4H-[1,2,4]triazol-3-yl]-cyclopropyl}-3-methyl-piperidin-1-yl)-2-hydroxy-2-methyl-propan-1-one |
| "A18" | (R)-3,3,3-Trifluoro-1-((3R,4R)-4-{1-[5-(4-fluoro-phenyl)-4H-[1,2,4]triazol-3-yl]-cyclopropyl}-3-methyl-piperidin-1-yl)-2-hydroxy-2-methyl-propan-1-one |
| "A19" | (R)-3,3,3-Trifluoro-1-((3S,4S)-4-{1-[5-(4-fluoro-phenyl)-4H-[1,2,4]triazol-3-yl]-cyclopropyl}-3-methyl-piperidin-1-yl)-2-hydroxy-2-methyl-propan-1-one |
| "A20" | (R)-3,3,3-Trifluoro-2-hydroxy-2-methyl-1-{3-methyl-4-[1-(5-p-tolyl-4H-[1,2,4]triazol-3-yl)-cyclopropyl]-piperidin-1-yl}-propan-1-one |
| "A21" | (R)-3,3,3-Trifluoro-2-hydroxy-2-methyl-1-{(3R,4R)-3-methyl-4-[1-(5-p-tolyl-4H-[1,2,4]triazol-3-yl)-cyclopropyl]-piperidin-1-yl}-propan-1-one |
| "A22" | (R)-3,3,3-Trifluoro-2-hydroxy-2-methyl-1-{(3S,4S)-3-methyl-4-[1-(5-p-tolyl-4H-[1,2,4]triazol-3-yl)-cyclopropyl]-piperidin-1-yl}-propan-1-one |
| "A23" | (R)-3,3,3-Trifluoro-2-hydroxy-2-methyl-1-{3-methyl-4-[1-(5-p-tolyl-[1,3,4]oxadiazol-2-yl)-cyclopropyl]-piperidin-1-yl}-propan-1-one |
| "A24" | (R)-3,3,3-Trifluoro-2-hydroxy-2-methyl-1-{(3R,4R)-3-methyl-4-[1-(5-p-tolyl-[1,3,4]oxadiazol-2-yl)-cyclopropyl]-piperidin-1-yl}-propan-1-one |
| "A25" | (R)-3,3,3-Trifluoro-2-hydroxy-2-methyl-1-{(3S,4S)-3-methyl-4-[1-(5-p-tolyl-[1,3,4]oxadiazol-2-yl)-cyclopropyl]-piperidin-1-yl}-propan-1-one |
| "A26" | (R)-3,3,3-Trifluoro-2-hydroxy-1-(4-{1-[5-(4-methoxy-phenyl)-4H-[1,2,4]triazol-3-yl]-cyclopropyl}-3-methyl-piperidin-1-yl)-2-methyl-propan-1-one |
| "A27" | (R)-3,3,3-Trifluoro-2-hydroxy-1-((3R,4R)-4-{1-[5-(4-methoxy-phenyl)-4H-[1,2,4]triazol-3-yl]-cyclopropyl}-3-methyl-piperidin-1-yl)-2-methyl-propan-1-one |
| "A28" | (R)-3,3,3-Trifluoro-2-hydroxy-1-((3S,4S)-4-{1-[5-(4-methoxy-phenyl)-4H-[1,2,4]trizaol-3-yl]-cyclopropyl}-3-methyl-piperidin-1-yl)-2-methyl-propan-1-one |
| "A29" | (R)-3,3,3-Trifluoro-2-hydroxy-1-(4-{1-[5-(4-methoxy-phenyl)-[1,3,4]oxadizaol-2-yl]-cyclopropyl}-3-methyl-piperidin-1-yl)-2-methyl-propan-1-one |
| "A30" | (R)-3,3,3-Trifluoro-2-hydroxy-1-((3R,4R)-4-{1-[5-(4-methoxy-phenyl)-[1,3,4]oxadiazol-2-yl]-cyclopropyl}-3-methyl-piperidin-1-yl)-2-methyl-propan-1-one |
| "A31" | (R)-3,3,3-Trifluoro-2-hydroxy-1-((3S,4S)-4-{1-[5-(4-methoxy-phenyl)-[1,3,4]oxadiazol-2-yl]-cyclopropyl}-3-methyl-piperidin-1-yl)-2-methyl-propan-1-one |
| "A32" | (R)-1-(4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one |
| "A33" | (R)-1-((3R,4R)-4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one |
| "A34" | (R)-1-((3S,4S)-4-{1-[5-(4-Chloro-phenyl)-4H-[1,2,4]triazol-3-yl]-cyclopropyl}-3-methyl-piperidin-1-yl)-3,3,3-trifluoro-2-hydroxy-2-methyl-propan-1-one |
| "A35" | (R)-1-(4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one |

-continued

| No. | Name |
|---|---|
| "A36" | (R)-1-((3R,4R)-4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one |
| "A37" | (R)-1-((3S,4S)-4-{1-[5-(4-Chloro-phenyl)-[1,3,4]oxadiazol-2-yl]-cyclopropyl}-3-methyl-piperidin-1-yl)-3,3,3-trifluoro-2-hydroxy-2-methyl-propan-1-one |
| "A38" | (R)-3,3,3-Trifluoro-2-hydroxy-1-(4-{1-[5-(6-methoxy-pyridin-3-yl)-4H-[1,2,4]triazol-3-yl]-cyclopropyl}-3-methyl-piperidin-1-yl)-2-methyl-propan-1-one |
| "A39" | (R)-3,3,3-Trifluoro-2-hydroxy-1-((3R,4R)-4-{1-[5-(6-methoxy-pyridin-3-yl)-4H-[1,2,4]triazol-3-yl]cyclopropyl}-3-methyl-piperidin-1-yl)-2-methyl-propan-1-one |
| "A40" | (R)-3,3,3-Trifluoro-2-hydroxy-1-((3S,4S)-4-{1-[5-(6-methoxy-pyridin-3-yl)-4H-[1,2,4]triazol-3-yl]-cyclopropyl}-3-methyl-piperidin-1-yl)-2-methyl-propan-1-one |
| "A41" | (R)-3,3,3-Trifluoro-2-hydroxy-1-(4-{1-[5-(6-methoxy-pyridin-3-yl)-[1,3,4]oxadizaol-2-yl]-cyclopropyl}-3-methyl-piperidin-1-yl)-2-methyl-propan-1-one |
| "A42" | (R)-3,3,3-Trifluoro-2-hydroxy-1-((3R,4R)-4-{1-[5-(6-methoxy-pyridin-3-yl)-[1,3,4]oxadiazol-2-yl]-cyclopropyl}-3-methyl-piperidin-1-yl)-2-methyl-propan-1-one |
| "A43" | (R)-3,3,3-Trifluoro-2-hydroxy-1-((3S,4S)-4-{1-[5-(6-methoxy-pyridin-3-yl)-[1,3,4]oxadiazol-2-yl]-cyclopropyl}-3-methyl-piperidin-1-yl)-2-methyl-propan-1-one | and pharmaceutically acceptable salts, tautomers and stereoisomers thereof, including mixtures thereof in all ratios.

11. A process for the preparation of a compound of the formula I according to claim 1 and pharmaceutically acceptable salts, tautomers and stereoisomers thereof,
wherein X denotes NH,
wherein
a compound of the formula II

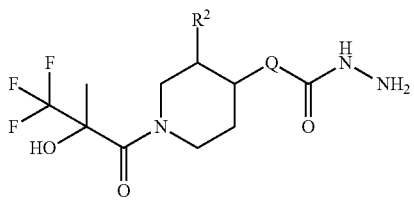

in which
Q denotes $C(CH_3)_2$ or 1,1-cyclopropylene,
$R^2$ denotes H or $CH_3$,
is reacted with a compound of the formula III

    III in which
$R^1$ denotes H, A, Cyc, Ar or Het,
and/or
a base or acid of the formula I is converted into one of its salts.

12. A pharmaceutical composition comprising at least one compound of the formula I according to claim 1 and/or a pharmaceutically acceptable salt, tautomer or stereoisomer thereof, including mixtures thereof in all ratios, and optionally a pharmaceutically acceptable carrier, excipient or vehicle.

13. A method for treating cancer or diabetes comprising administering a compound of the formula I according to claim 1 and/or a pharmaceutically acceptable salt, tautomer or stereoisomer thereof, including mixtures thereof in all ratios.

14. A method for treating cancer comprising administering a pharmaceutical composition according to claim 12.

15. A pharmaceutical composition comprising at least one compound of the formula I according to claim 1 and/or a pharmaceutically acceptable salt, tautomer or stereoisomer thereof, including mixtures thereof in all ratios, and at least one further active ingredient.

16. A set (kit) consisting of separate packs of
(a) an effective amount of a compound of the formula I according to claim 1 and/or a pharmaceutically acceptable salt, tautomer and or stereoisomer thereof, including mixtures thereof in all ratios, and
(b) an effective amount of a further active ingredient.

17. A method of inhibiting PDHK comprising administering a compound of the formula I according to claim 1 and/or a pharmaceutically acceptable salt, tautomer or stereoisomer thereof, including mixtures thereof in all ratios.

* * * * *